United States Patent
Ashida et al.

(10) Patent No.: US 12,208,113 B2
(45) Date of Patent: *Jan. 28, 2025

(54) METHOD FOR SELECTING CELLS, METHOD FOR PRODUCING NUCLEIC ACID, METHOD FOR PRODUCING RECOMBINANT CELLS, METHOD FOR PRODUCING TARGET SUBSTANCE, METHOD FOR PRODUCING PHARMACEUTICAL COMPOSITION, AND REAGENT

(71) Applicant: NB HEALTH LABORATORY CO., LTD., Sapporo (JP)

(72) Inventors: Masami Ashida, Sapporo (JP); Yuji Urushibata, Sapporo (JP); Kiyoshi Takayama, Sapporo (JP)

(73) Assignee: NB HEALTH LABORATORY CO., LTD., Sapporo (JP)

( * ) Notice: Subject to any disclaimer, the term of this patent is extended or adjusted under 35 U.S.C. 154(b) by 373 days.

This patent is subject to a terminal disclaimer.

(21) Appl. No.: 17/742,042

(22) Filed: May 11, 2022

(65) Prior Publication Data

US 2022/0347202 A1 Nov. 3, 2022

Related U.S. Application Data

(63) Continuation of application No. 17/431,268, filed as application No. PCT/JP2020/006069 on Feb. 17, 2020, now Pat. No. 11,357,787.

(30) Foreign Application Priority Data

Feb. 18, 2019 (JP) ................................ 2019-026766

(51) Int. Cl.
| | | |
|---|---|---|
| A61K 31/7088 | (2006.01) | |
| A61P 37/04 | (2006.01) | |
| C07K 16/28 | (2006.01) | |
| C12N 5/12 | (2006.01) | |
| C12N 15/62 | (2006.01) | |
| C12N 15/85 | (2006.01) | |
| C12P 21/02 | (2006.01) | |
| G01N 33/533 | (2006.01) | |

(52) U.S. Cl.
CPC .......... *A61K 31/7088* (2013.01); *A61P 37/04* (2018.01); *C07K 16/28* (2013.01); *C12N 5/12* (2013.01); *C12N 15/62* (2013.01); *C12N 15/85* (2013.01); *C12P 21/02* (2013.01); *G01N 33/533* (2013.01)

(58) Field of Classification Search
None
See application file for complete search history.

(56) References Cited

U.S. PATENT DOCUMENTS

| | | |
|---|---|---|
| 2004/0058395 A1 | 3/2004 | Hara |
| 2007/0111201 A1 | 5/2007 | Doranz |
| 2011/0294678 A1 | 12/2011 | Jin et al. |
| 2012/0015824 A1 | 1/2012 | Love et al. |
| 2012/0149592 A1 | 6/2012 | Love et al. |
| 2018/0282677 A1 | 10/2018 | Ohsaka et al. |

FOREIGN PATENT DOCUMENTS

| | | |
|---|---|---|
| JP | 2003-522948 | 7/2003 |
| JP | 2004-173681 | 6/2004 |
| JP | 2005-261339 | 9/2005 |
| JP | 4148367 | 9/2008 |
| JP | 2009-34047 | 2/2009 |
| JP | 2010-281595 | 12/2010 |
| JP | 2012-511155 | 5/2012 |
| JP | 2012-515548 | 7/2012 |
| JP | 2014-110785 | 6/2014 |
| WO | 01/59457 | 8/2001 |
| WO | 02/37099 | 5/2002 |
| WO | 2004/051268 | 6/2004 |
| WO | 2010/065929 | 6/2010 |
| WO | 2010/085275 | 7/2010 |
| WO | 2012/043634 | 4/2012 |
| WO | 2012/072823 | 6/2012 |

(Continued)

OTHER PUBLICATIONS

Extended European Search Report issued Oct. 26, 2022 in corresponding European Patent Application No. 20760277.2 (corresponding to U.S. Appl. No. 17/431,268).

(Continued)

*Primary Examiner* — Michael D Burkhart

(74) *Attorney, Agent, or Firm* — Wenderoth, Lind & Ponack, L.L.P.

(57) ABSTRACT

To provide a technique for selecting a target cell producing a target substance that specifically binds to a desired cell membrane protein more rapidly and efficiently. A substrate 1 having a plurality of microwells 2 is provided. A first cell 3 expressing a target cell membrane protein on its surface is allowed to adhere to each of the microwells 2. One or two second cells 5 as a candidate of a target cell are introduced into each microwell 2, and are allowed to coexist with the first cell 3 in the microwell 2, and target substance 6 secreted by the second cell 5 is brought into contact with the first cell 3. A microwell 2 including the first cell 3 to which the target substance 6 binds is identified. The second cell 5 as the target cell is recovered from the identified microwell 2. One example of the target substance 6 is an antibody. Visualization may be performed by adding a label substance 7.

21 Claims, 9 Drawing Sheets

Specification includes a Sequence Listing.

(56) References Cited

FOREIGN PATENT DOCUMENTS

WO  2017/057234  4/2017
WO  2018/175917  9/2018

OTHER PUBLICATIONS

International Search Report issued Apr. 21, 2020 in International (PCT) Application No. PCT/JP2020/006069.
Fitzgerald, V. et al., "Single cell selecting approaches for antibody discovery", Methods 116:34-42, 2017.
Shembekar, N. et al., "Single-Cell Droplet Microfluidic Screening for Antibodies Specifically Binding to Target Cells", Cell Reports 22, 2206-2215, 2018.
Yoshimoto, N. et al., "Development of automated single-cell isolation and analysis system -Review", Seibutsu-kogaku, 89: 72-78, 2011.
International Preliminary Report on Patentability issued Aug. 10, 2021 in International (PCT) Application No. PCT/JP2020/006069.
Yang, Z., et al., "A cell-cell interaction format for selection of high-affinity antibodies to membrane proteins", PNAS, 2019, vol. 116, pp. 14971-14978.

SEQUENCE LISTING

<160> NUMBER OF SEQ ID NOS: 8

<210> SEQ ID NO 1
<211> LENGTH: 1164
<212> TYPE: DNA
<213> ORGANISM: Artificial Sequence
<220> FEATURE:
<223> OTHER INFORMATION: artificial gene
<220> FEATURE:
<221> NAME/KEY: CDS
<222> LOCATION: (12)..(1154)

<400> SEQUENCE: 1

```
aagctagcgc c atg gag gag gga gga gat ttc gat aac tac tac ggc gct         50
             Met Glu Glu Gly Gly Asp Phe Asp Asn Tyr Tyr Gly Ala
               1               5                  10 gac aac cag agc gag tgt gag tac acc gac tgg aag agc agc gga gct          98
Asp Asn Gln Ser Glu Cys Glu Tyr Thr Asp Trp Lys Ser Ser Gly Ala
 15                  20                  25 ctc atc cct gca atc tac atg ctc gtg ttc ctc ctg gga act acc gga         146
Leu Ile Pro Ala Ile Tyr Met Leu Val Phe Leu Leu Gly Thr Thr Gly
30                  35                  40                  45 aac gga ctg gtg ctc tgg act gtc ttt aga agc agc aga gag aag agg         194
Asn Gly Leu Val Leu Trp Thr Val Phe Arg Ser Ser Arg Glu Lys Arg
                 50                  55                  60 agg tcc gca gat atc ttc atc gcc tcc ctg gca gtc gct gat ctc act         242
Arg Ser Ala Asp Ile Phe Ile Ala Ser Leu Ala Val Ala Asp Leu Thr
             65                  70                  75 ttc gtc gtc aca ctg cca ctg tgg gca aca tat acc tac agg gat tac         290
Phe Val Val Thr Leu Pro Leu Trp Ala Thr Tyr Thr Tyr Arg Asp Tyr
         80                  85                  90 gac tgg cca ttc gga acc ttc ttc tgc aag ctg tcc tcc tac ctc atc         338
Asp Trp Pro Phe Gly Thr Phe Phe Cys Lys Leu Ser Ser Tyr Leu Ile
     95                 100                 105 ttc gtg aac atg tac gcc tcc gtg ttc tgc ctc acc gga ctg tcc ttc         386
Phe Val Asn Met Tyr Ala Ser Val Phe Cys Leu Thr Gly Leu Ser Phe
110                 115                 120                 125 gat agg tac ctg gca atc gtg agg cct gtc gca aac gca aga ctg agg         434
Asp Arg Tyr Leu Ala Ile Val Arg Pro Val Ala Asn Ala Arg Leu Arg
                130                 135                 140 ctg aga gtg agc ggg gcc gtg gct aca gct gtg ctg tgg gtg ctc gct         482
Leu Arg Val Ser Gly Ala Val Ala Thr Ala Val Leu Trp Val Leu Ala
            145                 150                 155 gct ctg ctc gct atg cca gtc atg gtg ctg aga act act ggc gat ctg         530
Ala Leu Leu Ala Met Pro Val Met Val Leu Arg Thr Thr Gly Asp Leu
            160                 165                 170 gaa aat act aca aag gtg caa tgt tat atg gac tac tcc atg gtg gct         578
Glu Asn Thr Thr Lys Val Gln Cys Tyr Met Asp Tyr Ser Met Val Ala
        175                 180                 185 act gtc agc agc gaa tgg gcc tgg gaa gtg ggc ctg ggc gtg tcc agc         626
Thr Val Ser Ser Glu Trp Ala Trp Glu Val Gly Leu Gly Val Ser Ser
190                 195                 200                 205 act aca gtg ggc ttt gtc gtg cct ttt aca att atg ctc aca tgt tac         674
Thr Thr Val Gly Phe Val Val Pro Phe Thr Ile Met Leu Thr Cys Tyr
                210                 215                 220 ttc ttc atc gcc caa aca atc gcc ggg cat ttc agg aag gaa agg atc         722
Phe Phe Ile Ala Gln Thr Ile Ala Gly His Phe Arg Lys Glu Arg Ile
            225                 230                 235 gag ggc ctc aga aag agg aga aga ctc ctg tcc att att gtg gtc ctg         770
Glu Gly Leu Arg Lys Arg Arg Arg Leu Leu Ser Ile Ile Val Val Leu
            240                 245                 250
```

-continued

| | | | | | | | | | | | | | | | | |
|---|---|---|---|---|---|---|---|---|---|---|---|---|---|---|---|---|
|gtg|gtc|acc|ttc|gcc|ctc|tgt|tgg|atg|cct|tac|cac|ctg|gtg|aaa|acc|818|
|Val|Val|Thr|Phe|Ala|Leu|Cys|Trp|Met|Pro|Tyr|His|Leu|Val|Lys|Thr||
||255|||||260|||||265|||||

| | | | | | | | | | | | | | | | | |
|---|---|---|---|---|---|---|---|---|---|---|---|---|---|---|---|---|
|ctc|tat|atg|ctg|ggg|tcc|ctg|ctg|cat|tgg|cca|tgt|gac|ttt|gac|ctc|866|
|Leu|Tyr|Met|Leu|Gly|Ser|Leu|Leu|His|Trp|Pro|Cys|Asp|Phe|Asp|Leu||
|270||||||275||||280|||||285|

| | | | | | | | | | | | | | | | | |
|---|---|---|---|---|---|---|---|---|---|---|---|---|---|---|---|---|
|ttt|ctc|atg|aac|att|ttt|cct|tat|tgc|acc|tgc|att|tcc|tat|gtc|aat|914|
|Phe|Leu|Met|Asn|Ile|Phe|Pro|Tyr|Cys|Thr|Cys|Ile|Ser|Tyr|Val|Asn||
||||290|||||295|||||300|||

| | | | | | | | | | | | | | | | | |
|---|---|---|---|---|---|---|---|---|---|---|---|---|---|---|---|---|
|tcc|tgc|ctg|aat|ccc|ttt|ctg|tat|gcc|ttt|ttt|gac|ccc|agg|ttt|aga|962|
|Ser|Cys|Leu|Asn|Pro|Phe|Leu|Tyr|Ala|Phe|Phe|Asp|Pro|Arg|Phe|Arg||
||||305||||310|||||315|||

| | | | | | | | | | | | | | | | | |
|---|---|---|---|---|---|---|---|---|---|---|---|---|---|---|---|---|
|cag|gcc|tgc|acc|agc|atg|ctg|tgt|tgc|ggc|cag|tcc|aga|tgt|gcc|ggg|1010|
|Gln|Ala|Cys|Thr|Ser|Met|Leu|Cys|Cys|Gly|Gln|Ser|Arg|Cys|Ala|Gly||
|||320|||||325||||330||||

| | | | | | | | | | | | | | | | | |
|---|---|---|---|---|---|---|---|---|---|---|---|---|---|---|---|---|
|acc|tcc|cac|agc|tcc|agc|ggc|gag|aaa|tcc|gcc|tcc|tat|agc|agc|ggg|1058|
|Thr|Ser|His|Ser|Ser|Ser|Gly|Glu|Lys|Ser|Ala|Ser|Tyr|Ser|Ser|Gly||
||335|||||340|||||345||||

| | | | | | | | | | | | | | | | | |
|---|---|---|---|---|---|---|---|---|---|---|---|---|---|---|---|---|
|cac|agc|cag|ggg|ccc|ggc|ccc|aat|atg|ggg|aaa|ggg|ggc|gaa|cag|atg|1106|
|His|Ser|Gln|Gly|Pro|Gly|Pro|Asn|Met|Gly|Lys|Gly|Gly|Glu|Gln|Met||
|350||||355|||||360|||||365||

| | | | | | | | | | | | | | | |
|---|---|---|---|---|---|---|---|---|---|---|---|---|---|---|---|
|cac|gaa|aaa|agc|att|ccc|tat|agc|cag|gag|aca|ctg|gtc|gtg|gac|tga|1154|
|His|Glu|Lys|Ser|Ile|Pro|Tyr|Ser|Gln|Glu|Thr|Leu|Val|Val|Asp|||
||||370|||||375|||||380|| tagtcgacac  1164

<210> SEQ ID NO 2
<211> LENGTH: 380
<212> TYPE: PRT
<213> ORGANISM: Artificial Sequence
<220> FEATURE:
<223> OTHER INFORMATION: artificial gene

<400> SEQUENCE: 2

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60
Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

-continued

```
Ser Glu Trp Ala Trp Glu Val Gly Leu Gly Val Ser Ser Thr Thr Val
        195                 200                 205
Gly Phe Val Val Pro Phe Thr Ile Met Leu Thr Cys Tyr Phe Phe Ile
    210                 215                 220
Ala Gln Thr Ile Ala Gly His Phe Arg Lys Glu Arg Ile Glu Gly Leu
225                 230                 235                 240
Arg Lys Arg Arg Arg Leu Leu Ser Ile Ile Val Val Leu Val Val Thr
                245                 250                 255
Phe Ala Leu Cys Trp Met Pro Tyr His Leu Val Lys Thr Leu Tyr Met
            260                 265                 270
Leu Gly Ser Leu Leu His Trp Pro Cys Asp Phe Asp Leu Phe Leu Met
        275                 280                 285
Asn Ile Phe Pro Tyr Cys Thr Cys Ile Ser Tyr Val Asn Ser Cys Leu
    290                 295                 300
Asn Pro Phe Leu Tyr Ala Phe Phe Asp Pro Arg Phe Arg Gln Ala Cys
305                 310                 315                 320
Thr Ser Met Leu Cys Cys Gly Gln Ser Arg Cys Ala Gly Thr Ser His
                325                 330                 335
Ser Ser Ser Gly Glu Lys Ser Ala Ser Tyr Ser Ser Gly His Ser Gln
            340                 345                 350
Gly Pro Gly Pro Asn Met Gly Lys Gly Gly Glu Gln Met His Glu Lys
        355                 360                 365
Ser Ile Pro Tyr Ser Gln Glu Thr Leu Val Val Asp
    370                 375                 380

<210> SEQ ID NO 3
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (37)..(37)
<223> OTHER INFORMATION: n stands for a, g, c or t

<400> SEQUENCE: 3
gctagcgcta ccggactcag atccccccccc ccccdn                               37

<210> SEQ ID NO 4
<211> LENGTH: 23
<212> TYPE: DNA
<213> ORGANISM: Artificial Sequence
<220> FEATURE:
<223> OTHER INFORMATION: primer Sequence

<400> SEQUENCE: 4
accytgcatt tgaactcctt gcc                                              23

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
actgccatca atcttccact tgaca                                            25

<210> SEQ ID NO 6
```

```
<211> LENGTH: 44
<212> TYPE: DNA
<213> ORGANISM: Artificial Sequence
<220> FEATURE:
<223> OTHER INFORMATION: primer

<400> SEQUENCE: 6
ggtttagtga accgtcagat ccgctagcgc taccggactc agat                    44

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
ctggacaggg atccagagtt cca                                           23

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
actgaggcac ctccagatgt taact                                         25
```

METHOD FOR SELECTING CELLS, METHOD FOR PRODUCING NUCLEIC ACID, METHOD FOR PRODUCING RECOMBINANT CELLS, METHOD FOR PRODUCING TARGET SUBSTANCE, METHOD FOR PRODUCING PHARMACEUTICAL COMPOSITION, AND REAGENT

CROSS-REFERENCE TO RELATED APPLICATION

This application is a Continuation of U.S. application Ser. No. 17/431,268, filed on Aug. 16, 2021, which is a National Phase under 35 U.S.C. § 371 of International Application No. PCT/JP2020/006069, filed on Feb. 17, 2020, which claims the benefit of priority of Japanese Patent Application No. 2019-026766, filed on Feb. 18, 2019, the entire contents of which are incorporated herein by reference.

A sequence listing in electronic (ASCII text file) format is filed with this application and incorporated herein by reference. The name of the ASCII text file is "2022-0715-sequence-listing.txt"; the file was created on Jul. 15, 2022; the size of the file is 10,505 bytes.

TECHNICAL FIELD

The present invention relates to a method for selecting a cell, a method for producing nucleic acid, a method for producing a recombinant cell, a method for producing a target substance, a method for producing a pharmaceutical composition, and a reagent.

BACKGROUND ART

Cell membrane proteins such as G protein-coupled receptors (GPCRs), transporters, ion channels, and cytokine receptors are known to be involved in various diseases, and are attracting attention as target molecules for diagnostic agents and medical drugs. When the cell membrane protein binds to a ligand composed of an extracellular substance, for example, a low molecular weight compound, a peptide, a protein, or the like, and the function thereof is activated or inhibited, so that a cell function and a pharmacological function are expressed.

In addition, in recent years, specific antibodies and antibody-like molecules (antibody fragments, single-chain antibodies, bispecific antibodies, drug-conjugated antibodies, or the like) binding to cell membrane proteins have attracted attention, and being developed as diagnostic agents or medical drugs.

Specific binding substances (for example, protein ligands, peptide ligands, specific antibodies, and the like) against cell membrane proteins, in particular, multiple transmembrane protein (for example, GPCR, transporter, ion channel, and the like) are being developed as pharmaceutical product. However, the specific binding substances that have been practically used as pharmaceutical products are limited.

Isolation and purification of the multiple transmembrane protein are especially difficult because the multiple transmembrane protein includes more hydrophobic structures than soluble proteins (for example, cytokines, hormones, enzymes, and nuclear receptors). In addition, instances of purification which has been proved to be able to maintain a structure present in the natural world, and maintain a function of the multiple transmembrane protein are limited. In general, the multiple transmembrane protein exhibits the functionality in a state in which the multiple transmembrane protein exists in a lipid bilayer.

Examples of techniques for searching a specific binding substance against cell membrane proteins include a method using a purified peptide produced in large amounts, the purified peptide corresponding to a part of the cell membrane protein which is an extracellularly exposed soluble domain or partial peptide. For example, the method includes immobilizing the purified soluble domain or partial peptide on a 96-well plate, and evaluating binding to a candidate specific binding substance by an EUSA method or the like. However, it is not secured that the substance selected by such a method binds to the target cell membrane protein existing in the living body specifically and with high affinity. Therefore, when searching for a useful specific binding substance for a cell membrane protein for the purpose of developing a diagnostic agent or a medical drug, in order to imitate the three-dimensional structure of the cell membrane protein in vivo, it is more effective to use mammalian cells, in which a target cell membrane protein is expressed on the cell membrane of a living cell.

On the other hand, substances such as peptide ligands, protein ligands, and specific antibodies can be secreted into a culture supernatant by culturing human or non-human cells or recombinant cells using gene recombination technology. Herein, when discovering an unknown substance that specifically binds to a target cell membrane protein, it is necessary to examine a population of thousands to tens of thousands of kinds of producing cells that produce different substances (for example, an antibody-producing hybridoma library). However, in recent years, the number of producing cells to be examined in order to search for new substances has tended to increase. Examination of tens of thousands to tens of millions of kinds of cells may be necessary. Accordingly, conventional technologies have large problems in terms of cost required for culturing and maintaining producing cells, a time required for searching thereof, and the like.

Conventional technologies for searching a specific antibody against a desired cell membrane protein include a technique combining culturing of hybridomas and a flow cytometer. For example, culture supernatants of thousands of hybridomas are prepared, and brought into contact with CHO cells expressing the target cell membrane protein on the cell surface, and the binding thereof is evaluated by using a flow cytometer. Then, the hybridomas determined to be positive are recovered and further cultured by the limiting dilution method. Then, the binding evaluation using a flow cytometer is repeated, and the cells producing a desired specific antibody can be identified over about two months (see, for example. Patent Document 1).

However, it is known that when a non-human animal is immunized with a cell membrane protein such as GPCR as an antigen, the frequency of appearance of an antibody having high affinity and specificity is very low. In order to select a target cell producing specific antibodies having such a low frequency of appearance, the hybridoma method needs to culture and evaluate hundreds of thousands to several millions kinds of producing cells. Accordingly, it is considered that the conventional method using culturing of hybridomas and a flow cytometer is approaching the limit of ability.

As another technique, a method for identifying a specific antibody-producing cell, which applies a single cell analysis technique, is being developed (Non-Patent Document 1). For example, one antibody-producing cell and antigen protein are contained in a hydrophobic microdroplet. Then, the presence or absence of binding between the antibody secreted from the antibody-producing cells and the antigen protein can be visualized, and microdroplets including a positive cell producing a specific antibody can be separated in an analytical instrument having a microfluidics.

Non-Patent Document 2 describes the principle of a method, using microdroplet and microfluidics, for identifying a specific antibody-producing cell.

However, this method cannot add a washing step in the process of visualizing the presence or absence of binding between an antibody and an antigen protein in the microdroplet. Accordingly, when targeting a cell membrane protein in which an amount expressed on the cell membrane surface is very small, it has been reported that it is difficult to demonstrate the presence or absence of the binding because the fluorescence signal by the binding between the antibody and the antigen protein is weaker as compared with the background fluorescence signal (Non-Patent Document 1).

Furthermore, it is very difficult to maintain survival of a cell in a microdroplet, especially to maintain survival of non-immortalized B lymphocytes and plasma cells derived from bone marrow tissue, spleen, lymphatic tissue, or blood, so that strict control for each cell type is required.

In addition, in general, a plurality of negative antibody-producing cells are also included in the microdroplet including positive cells. Therefore, in order to establish a monoclonal antibody, it is necessary to perform a screening operation multiple times.

Furthermore, methods for visualizing the presence or absence of binding between the antibody and the target cell membrane protein need to be optimized for each target cell membrane protein, and remain to be improved for general use.

Patent Document 2 describes a technique for bringing a cell population expressing a target cell membrane protein into contact with a candidate cell population on a slide glass, and identifying a cell producing an antibody against a target cell membrane protein from the candidate cell population. However, this method also cannot include the washing step mentioned above. Accordingly, when targeting a cell membrane protein in which an amount expressed on the cell membrane surface is very small, it is difficult to confirm the presence or absence of binding between the antibody and the cell membrane protein.

Patent Document 3 discloses a technique for introducing candidates of antibody-producing cells into microwells coated with purified soluble cytokine receptor protein, and selecting a desired antibody-producing cell by the detection of the binding between the antibody secreted by the cell and the soluble cytokine receptor protein. However, as described above, the isolated and purified receptor protein does not always maintain a structure that exhibits its function in vivo. In addition, it is very difficult to apply this method to multiple transmembrane proteins that are difficult to be purified.

PRIOR ART DOCUMENTS

Patent Documents

Patent Document 1: WO 2012/043634
Patent Document 2: WO 2004/051268
Patent Document 3: JP 4148367 B Non-Patent Documents Non-Patent Document 1: Fitzgerald V, Leonard P., "Single cell selecting approaches for antibody discovery", Methods, 116:34-42, 2017

Non-Patent Document 2: Shembekar et al., "Single-Cell Droplet Microfluidic Screening for Antibodies Specifically Binding to Target Cells", Cell Reports 22, 2206-2215, Feb. 20, 2018

DISCLOSURE OF INVENTION

Technical Problem

As described above, it cannot be said that technique for selecting a cell producing a target substance that specifically binds to a cell membrane protein more quickly and efficiently has been completed. Furthermore, it is necessary to reduce the cell culture operation as much as possible in order to cope with the increase in the population of cells to be evaluated. Therefore, it is an object of the present invention to provide a technique for selecting a cell producing a target substance that specifically binds to a cell membrane protein more quickly and efficiently, and a technique for producing a target substance such as an antibody using the cell selected by the above technique.

Solution to Problem

The present inventors have found that when a cell expressing a target cell membrane protein and a candidate of a target cell producing a target substance that specifically binds to the cell membrane protein are allowed to coexist in a microwell having a diameter of 20 µm to 30 µm, the target cell can be selected in a very short time.

One aspect of the present invention is a method for selecting a target cell from a population of second cells, the target cell producing a target substance that specifically binds to a desired cell membrane protein, the method including:
  a) providing a substrate having a plurality of microwells;
  b) allowing a first cell to adhere to each of the microwells, the first cell expressing the cell membrane protein on its surface;
  c) following the step b), introducing one or two second cells isolated from the population into the each of the microwells, and allowing the first cell and the second cell to coexist in the each of the microwells;
  d) following the step c), identifying a microwell including a first cell to which the target substance binds; and
  e) recovering the second cell as the target cell from the microwell identified in the step d).

Preferably, the step d) includes a visualization step of visualizing binding of the target substance to the first cell.

Preferably, the visualization step includes adding a label substance that specifically binds to the target substance into the microwells.

Preferably, the label substance is a labeled antibody against the target substance.

Preferably, a label of the label substance is a fluorescent label.

Preferably, the label substance is an antibody labeled with a first fluorescent substance, the step b) includes a first cell labeling step of labeling the first cell adhering to the microwell with a second fluorescent substance, and a fluorescence wavelength of fluorescence emitted by a first fluorescent substance is different from a fluorescence wavelength of fluorescence emitted by a second fluorescent substance.

Preferably, the visualization step includes visualization of a change of an intracellular signaling molecule associated with activation of the cell membrane protein, occurring when the target substance binds to the first cell.

Preferably, the cell membrane protein is a multiple transmembrane protein.

Preferably, the first cell is a cell into which a vector expressing the cell membrane protein has been transfected.

Preferably, the first cell is a tumor cell expressing the cell membrane protein.

Preferably, the first cell is a non-tumor cell expressing the cell membrane protein.

Preferably, the target substance is an antibody.

Preferably, the second cell is derived from bone marrow, spleen, lymphatic tissue, or a blood cell derived from a non-human animal immunized with the cell membrane protein or a nucleic acid encoding the cell membrane protein.

Preferably, the second cell is an immortalized cell.

Preferably, the second cell is a hybridoma.

Preferably, the second cell is derived from human lymphatic tissue or blood.

Preferably, the second cell is a cell immortalized by Epstein-Barr virus infection.

Preferably, the second cell is a recombinant cell including an exogenous antibody gene and expressing the antibody.

Preferably, the antibody is a complete antibody, a functional antibody fragment, a single chain antibody, or a multispecific antibody.

Preferably, the antibody is a complete human antibody, a humanized antibody, or a chimeric antibody.

Preferably, the antibody is a felinized antibody or a caninized antibody.

Another aspect of the present invention is a method for producing a nucleic acid, the method including obtaining a nucleic acid encoding the target substance from a target cell selected from the population of second cells by the method described above.

Preferably, the target substance is an antibody.

Still another aspect of the present invention is a method for producing a recombinant cell, the method including transfecting a nucleic acid produced by the method described above into a host cell to obtain a recombinant cell expressing the target substance.

Yet another aspect of the present invention is a method for producing a target substance, the method including culturing a recombinant cell produced by the method described above to obtain a cultured product, and obtaining the target substance from the cultured product.

A further aspect of the present invention is a method for producing a target substance, the method including culturing a target cell selected from the population of second cells by the method described above to obtain a cultured product, and obtaining the target substance from the cultured product.

Preferably, the target substance is an antibody.

A still further aspect of the present invention is a pharmaceutical composition, the method including combining a pharmaceutically acceptable carrier or an additive with a nucleic acid produced by the method described above to obtain a pharmaceutical composition containing the nucleic acid as an active ingredient.

A yet further aspect of the present invention is a method for producing a pharmaceutical composition, the method including combining a pharmaceutically acceptable carrier or an additive with a target substance produced by the method described above to obtain a pharmaceutical composition containing the target substance as an active ingredient.

A further aspect of the present invention is a reagent for detecting the desired cell membrane protein, the reagent including a target substance produced by the method described above.

Effect of Invention

According to the present invention, a cell producing a target substance that specifically binds to a cell membrane protein can be selected quickly and more efficiently. Furthermore, a target substance that specifically binds to a cell membrane protein, for example, an antibody, can be easily produced.

BEST MODE FOR CARRYING OUT THE INVENTION

A cell selection method according to the present invention is a method for selecting a target cell producing a target substance that specifically binds to a desired cell membrane protein from a population of second cells. Hereinafter, the target cell may be referred to as a positive cell. The desired cell membrane protein may be referred to as "target cell membrane protein". The target substance may be referred to as "substance specifically binding to cell membrane protein", or may be simply referred to as "specific binding substance". Furthermore, in the present invention, the term "select a cell" can be paraphrased by "identify a cell".

Figure 1:
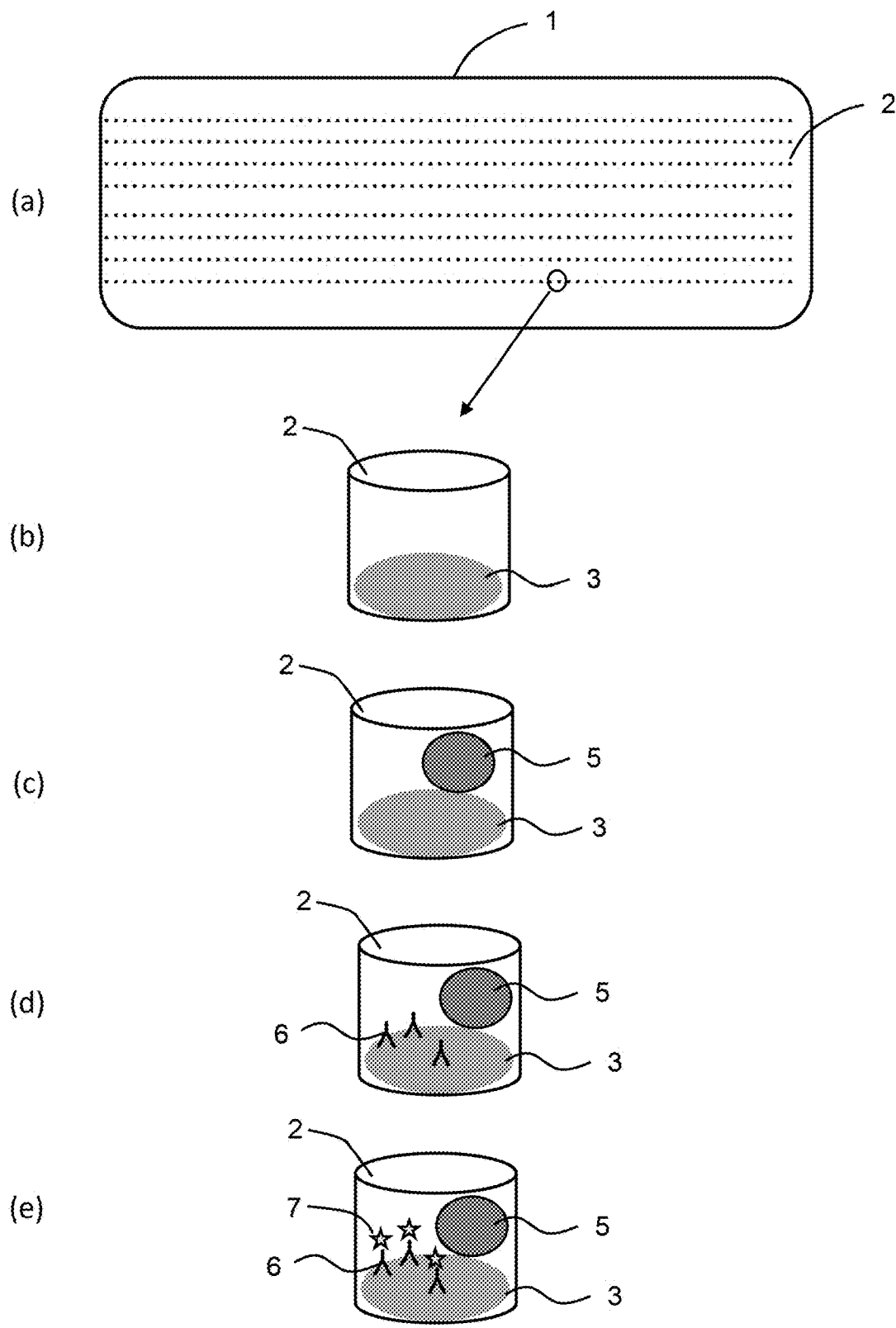
FIG. 1 is explanatory views showing an outline of a method for selecting cells according to one embodiment of the present invention, wherein (a) to (e) show each step.

FIG. 1 shows an outline of a cell selection method according to one embodiment of the present invention. FIG. 1(a) shows a substrate 1 having a plurality of microwells 2; FIG. 1(b) shows a state in which a first cell 3 is allowed to adhere to one of the microwells 2; FIG. 1(c) shows a state in which the first cell 3 is allowed to coexist with second cell 5 in the microwell 2; FIG. 1(d) shows a state in which target substances 6 secreted by the second cell 5 binds to the surface of the first cell 3; FIG. 1(e) shows a state in which label substances 7 binds to the target substances 6 on the surface of the first cell 3.

<Substrate and Microwell>

In the present invention, a substrate having a plurality of microwells is used. A microwell refers to a micro-sized well (dent, recess) containing about 1 to 3 mammalian or avian cells. The microwell is a bottomed minute hole having, for example, an inner diameter of the opening of about 10 μm to 50 μm, and a depth of about the same as the inner diameter of the opening.

The shape of the microwell is typically cylindrical. It may be a tubular shape composed of a plurality of planes, for example, a polygonal prism such as a square prism or a hexagonal prism, or a mortar shape such as an inverted cone or an inverted pyramid. Furthermore, the shape may be a shape in which two or more of these shapes are combined and connected. The case of an inverted cone or an inverted pyramid may be a shape in which the bottom surface of the cone is the opening of the microwell and a part of the apex is cut off (that is, a truncated cone or a truncated pyramid).

When the microwell is cylindrical, the diameter (inner diameter) of the opening can be appropriately determined in consideration of the type and number of cells to be accommodated in the microwell. When the first cell is a CHO cell, and the second cell is a non-human animal-derived B lymphocyte or a plasma cell, the diameter is preferably about 20 μm to 40 μm. Furthermore, the depth of the microwell is preferably about the same as the diameter of the opening.

The number of microwells per unit area (density) on the substrate is not particularly limited, and can be appropriately determined, for example, in consideration of the total number of second cells searched for each time and the expression frequency of target cells. For example, the number of microwells per $cm^2$ can be in the range of 20,000 to 200,000.

The distance (pitch) between the microwells on the substrate is not particularly limited, and can be appropriately set within a range that does not affect the adjacent microwells. For example, when the microwell is cylindrical, the distance between the centers of the opening portions of the adjacent microwells is preferably about 1.5 to 3 times as the opening diameter.

Materials of the substrate are not particularly limited, but transparent materials having no autofluorescence are preferable when the visualization step described later is performed.

A substrate having a plurality of microwells is commercially available. For example, substrate (microwell chambers) each having a plurality of microwells having a diameter of 10 μm, 20 μm, or 30 μm are commercially available from AS ONE Corporation.

<Target Cell Membrane Protein>

The target cell membrane protein in the present invention is not particularly limited, and includes all cell membrane proteins typified by a multiple transmembrane protein. Examples thereof include G protein-coupled receptors (GPCRs), ion channels, transporters, CD antigens, cell adhesion molecules, cancer antigens, viral antigens, and the like. Furthermore, the animal species from which the cell membrane protein is derived are not particularly limited. Furthermore, subjects of the present invention can include a cell membrane protein having situations that a purification method has not been established, mass purification is difficult, isolation and purification in a form maintaining a naturally occurring structure is difficult, and the like, wherein a part of the protein is extracellularly exposed from a lipid bilayer.

<First Cell>

In the present invention, a first cell expressing a desired cell membrane protein on the cell surface is used in a state in which the first cell is allowed to adhere to a microwell.

The first cell is not particularly limited as long as it can express a desired cell membrane protein on the cell surface. One embodiment includes a recombinant cell into which a vector expressing a target cell membrane protein has been transfected. For example, a gene of a full-length target cell membrane protein is inserted into an appropriate expression vector (for example, pcDNA, pEF/FRT/V5-DEST, etc.). Then, this vector is transfected into cells such as CHO cells, COS cells, HEK293 cells, and NIH3T3 cells, and the like, to obtain recombinant cells transiently or stably expressing the target cell membrane protein on the cell membrane. This recombinant cell can be used as the first cell. In this case, it is preferable that the expression level of the target cell membrane protein on the cell membrane is increased to five times or more as compared with a cell having no expression vector.

As another embodiment, tumor cells in which the target cell membrane protein is overexpressed as compared with normal cells can be used as the first cell. As the tumor cell, for example, a single cell from a surgically extirpated organ can be used. In addition, tumor cells are available from ATCC or cell distributors.

As still another embodiment, various cells (non-tumor cells) derived from normal tissue in which the target cell membrane protein expresses, for example, non-human or human tissue can be used as the first cell. For example, blood cells, nerve cells, vascular endothelial cells, vascular smooth muscle cells, immune cells, fat cells, skeletal muscle cells, lymphocyte cells, skin cells, and the like, can be used as the first cells. Furthermore, blood cells, which have been made into iPS by a well-known method and then differentiated into specific tissue cells, may be used as the first cell.

<Target Substance>

In the present invention, a target cell producing a target substance that specifically binds to a desired cell membrane protein is selected from a population of second cells. The target substance (specific binding substance) includes a polypeptide, a cyclic peptide, and a protein with a known or unknown structure, which selectively bind to a specific cell membrane protein. More specific examples include specific binding substances including peptide hormones, cytokines, antibodies, artificial polypeptides, artificial cyclic peptides, and the like.

<Second Cell>

In the present invention, a first cell and a second cell are allowed to coexist in a microwell. Hereinafter, the second cell will be specifically described.

Firstly, a case where a target substance (a specific binding substance) is a substance other than an antibody, in other words, an embodiment in which the second cell is other than an antibody-producing cell will be described.

The second cell is not particularly limited as long as it is a cell expected to produce a desired target substance. Examples of cells that can be used as the second cell include various cells derived from non-human or human tissues, for example, blood cells, nerve cells, vascular endothelial cells, vascular smooth muscle cells, immune cells, fat cells, skeletal muscle cells, lymphocyte cells, skin cells, and the like. For example, a cell obtained by separating a tissue of a non-human animal, and treating the tissue with collagenase, and the like, followed by being filtered through a mesh of 30 μm to 100 μm, and made into a single cell, can be used as a second cell. For example, a single cell from human blood or a surgically extirpated organ can be used as a second cell. In addition, tumor cells can be used as a second cell. As to the tumor cell, for example, a single cell made from a surgically extirpated organ can be used. Besides, tumor cells are available from ATCC or cell distributors.

Recombinant cells can be used as the second cell. For example, a cDNA library including a gene encoding a target substance is incorporated into an expression vector such as pcDNA, pEF/FRT/V5-DEST, Mammalian PowerExpress System, and the like. Then, this vector is transiently transfected into cells such as CHO cells, COS cells, HEK293 cells, and NSO cells to obtain recombinant cells. This recombinant cell can be used as the second cell. Furthermore, in the recombinant cells, the recombinant cells that have survived using drug resistance gene retained in the vector and constitutively expressing the gene can be used as the second cell. Furthermore, a cDNA library is incorporated into a viral vector derived from adenovirus, lentivirus, and the like, with which CHO cells. HEK293 cells, NIH3T3 cells, and the like, are infected, can be used as the second cell.

When a recombinant cell is used as the second cell, it is preferable that a gene encoding one kind of target substance is transfected into the recombinant cell.

Next, a case where a target substance (a specific binding substance) is an antibody, in other words, an embodiment in which the second cell is an antibody-producing cell will be described.

In the present invention, the term "antibody" may be replaced with "immunoglobulin". The antibody in the present invention includes a functional fragment thereof. Herein, "functional fragment of an antibody" refers to a partial fragment of an antibody (namely, immunoglobulin) having at least one interaction of an antigen. Examples of the partial fragments include F(ab')2, Fab, Fv, disulfide-bonded Fv, a single chain antibody (scFv, VH-VL), VH, and a polymer thereof, and a fused body of them and a heavy chain CH3 region. Furthermore, the antibody of the present invention may be a multispecific antibody. Examples thereof include a diabody that is one kind of a double-specific antibody (for example, WO 93/11161). The class (isotype) of the antibody of the present invention is not particularly limited. For example, it may be of any classes of IgG, IgM, IgA, IgD, IgE and the like. Furthermore, the subclass of the antibody is not particularly limited, and it may be of any subclasses including IgG1, IgG2, IgG3, IgG4 and the like, as far as it is IgG. Furthermore, the antibody may be any one of a complete human antibody, a humanized antibody, or a chimeric antibody.

Antibody-producing cells such as B cells and plasma cells derived from human lymphatic tissue and blood can be used as the second cell. For example, B cells and plasma cells collected from healthy subjects, patients with cancer, patients with known or unknown infectious diseases, patients with autoimmune diseases, vaccinated subjects, and the like, can be used as the second cell.

Note here that in order to identify antibody-producing cells against the target cell membrane protein more efficiently, cell concentration may be performed. For example, activated B cells or plasma cells obtained from bone marrow, spleen, lymphatic tissue, or blood cells from non-human animals immunized with the target cell membrane protein can be concentrated and used as a population of second cells. For example, activated B cells or plasma cells obtained from human lymphatic tissue or blood-derived cells are concentrated, and the concentrated cells can be used as a population of second cells. Concentration of activated B cells or plasma cells can be performed, for example, using the CD antigen on the cell surface as a label. For example, antibody magnetic beads against a specific CD antigen can be used. Examples of the CD antigens include CD2, CD3, CD4, CD8, CD11b, CD11c, CD14, CD15, CD16, CD34, CD40, CD43, CD45R, CD49b, CD56, CD61, CD79a, CD90.2, CD138, and CD235a. The level of the concentration includes, for example, concentration of activated B cells or plasma cells 50-fold or more from a population of about 10,000,000 lymphocyte cells derived from lymphatic tissues.

Examples of a method for immunizing non-human animals with a target cell membrane protein includes various methods like a method described in Hutchings C J, Koglin M. Olson W C, Marshall F H, "Opportunities for therapeutic antibodies directed at G-protein-coupled receptors", Nat Rev Drug Discov. 16(9), 2017. Examples thereof include a method of synthesizing a partial peptide or a partial protein exposed to the cell surface and using the synthesized product as an antigen for immunization. Another example is a method including solubilizing a target cell membrane protein from a cell with a detergent, purifying thereof, and immunizing using the obtained product as an antigen. Still another example is a method of directly immunizing a cell itself that highly expresses a target cell membrane protein. Furthermore, examples of the method include a method of immunizing an artificial bilayer or a virus-like nanoparticle in which a target cell membrane protein is presented as an antigen. Furthermore, examples include a method of immunizing a protein expression vector into which a cDNA sequence encoding a target cell membrane protein is inserted (DNA immunization). Among these methods, the DNA immunization is preferable because a more specific and high-affinity antibody can be obtained.

Immortalized cells such as hybridomas can be used as the second cell. For example, a hybridoma is obtained by collecting immune cells from a non-human animal immunized with a target cell membrane protein and fusing the immune cells with myeloma. The obtained hybridoma can be used as the second cell. For cell fusion, selection of hybridoma, and cloning, known methods can be used. For example, cell fusion can be performed by a method using polyethylene glycol, or a method of applying a voltage to a mixed solution of immune cells and myeloma. Further, the hybridoma can be selected by culturing using a HAT selective medium.

Cells can be immortalized by methods other than the hybridoma method. For example, in the case of B cells derived from human lymphatic tissue or blood, cells immortalized by Epstein-Barr virus infection can also be used as the second cell.

Recombinant cells into which an antibody gene has been transfected can be used as the second cell. For example, a cDNA library is prepared from B cells and plasma cells derived from lymphatic tissues and blood cells of immunized animals. From this cDNA library, a gene for an antibody or an antibody fragment is selectively amplified. The amplified gene is modified to prepare an antibody gene library so that various forms of antibody molecules such as a complete antibody, a functional antibody fragment, a single chain antibody, or a multispecific antibody can be expressed. This gene library is incorporated into a vector such as pcDNA, pEF/FRT/V5-DEST, Mammalian Power-Express System, and the like. Then, this vector is transiently transfected into cells such as CHO cells, COS cells, HEK293 cells, and NSO cells to obtain recombinant cells. This recombinant cell can be used as the second cell. Furthermore, in the recombinant cells, recombinant cells that have survived using the drug resistance gene retained in the vector and that constitutively express the gene can be used as the second cell.

The animal species from which the second cell is derived is not particularly limited, and mammalian cells or avian cells are preferably used. Examples of mammals include mice, rats, guinea pigs, rabbits, monkeys, cows, horses, dogs, cats, goats, sheep, pigs, camels, alpaca, and the like. Examples of avian include chickens, ducks and turkeys.

<Adhesion of First Cell>

In the present invention, the above-mentioned first cell is allowed to adhere to a microwell. Thus, the first cell can be accommodated and immobilized in the microwell in a state in which its cell function is not impaired. The number of first cells to be allowed to adhere to the microwell is not limited as long as a space for receiving a second cell can be secured, but the number is preferably 1 to 2.

<Coexistence of First Cell and Second Cell>

In the present invention, one or two second cells are introduced into a microwell to which the first cell adheres, and the first cell and the second cells are allowed to coexist. Thus, a target substance produced (secreted) by the second cell comes into contact with the surface of the first cell. It is preferable to introduce one second cell into the microwell.

It is preferable that after the first cell and the second cell are allowed to coexist, they are subjected to incubation under predetermined conditions. Incubation conditions can be determined, for example, in consideration of the property of the target substance produced by the second cell and the survival time of the second cell. For example, it is preferable that the incubation is performed in a phosphate buffer, HBSS, or a cell culture medium (for example, an RPMI medium, an HAM F-12 medium, and the like), into which bovine serum, growth factors, and cytokines (for example, IL-4, IL-5, IL-6, IL-13, IL-21, TNF, IFNγ, CD40 ligand, and the like) that enhance the production of specific binding agents are added as necessary, at 25° C. to 37° C. for 15 minutes to 6 hours.

<Identification of Positive Microwell>

After a first cell and a second cell are allowed to coexist in a microwell and incubated as necessary, the microwell including the first cell to which the target substance binds (positive microwell) is identified. In other words, in each microwell, the presence or absence of binding between the target cell membrane protein expressed on the surface of the first cell and the substance secreted from the second cell is detected.

As a method for detecting the presence or absence of the binding between the first cell and the target substance, for example, a visualization method is preferably used. In other words, a preferred embodiment includes a visualization step of visualizing binding of the specific binding substance to the first cell.

The technique of visualization is not particularly limited. One example is a direct technique of visualizing the surface of the first cell. Another example is an indirect technique of visualizing a change of an intracellular signaling molecule associated with activation of the cell membrane protein, occurring when the target substance binds to the first cell.

Examples of the direct technique include a method using a label substance that specifically binds to the target substance. In other words, the label substance is brought into contact with the first cell that coexists with the second cell in a microwell. The label substance is, for example, a labeled antibody.

Specific examples of procedures are described. Firstly, the above-mentioned cDNA library is designed such that the specific binding substance is provided with a tag (for example, FLAG, V5) or an Fc part of an antibody. A recombinant CHO cell or the like into which this cDNA library is transfected is used as the second cell. For the target substance to which the tag has been provided, a labeled antibody against the tag (for example, a labeled anti-FLAG antibody, a labeled anti-V5 antibody) can be used. A labeled anti-Fc antibody (for example, a labeled anti-IgG antibody) can be used for the target substance to which the Fc moiety is provided. As a specific operation, the first cell and the second cell are allowed to coexist in the microwell, then the cells are incubated under predetermined conditions as necessary, and then the label substance is added.

As the label, a label of a fluorescent substance (fluorescent complex), a fluorescent protein, an enzyme, or the like, can be employed.

Examples of the fluorescent substance include Alexa Fluor (registered trademark), Aqua, Texas Red (registered trademark), fluorescein and its derivatives, rhodamine and its derivatives, Cascade Blue (registered trademark), phycoerythrin, DyLight (registered trademark), and the like. Preferably. Alexa Fluor 488 is used.

Examples of the fluorescent protein include green fluorescent protein (GFP).

Examples of the enzyme include alkaline phosphatase, horseradish peroxidase, luciferase, and the like.

The first cell to which a target substance binds can be detected by using a strong signal emitted by the label substance (for example, a label antibody) as an indicator. Then, a microwell including a positive signal (positive microwell) can be identified by using a fluorescence microscope, a light emitting microscope, an inverted microscope, or an apparatus including these microscopic manipulation devices according to the characteristics of the label.

On the other hand, the indirect technique can be used when the specific binding substance is, for example, a substance which promotes the function of a cell membrane protein (for example, an endogenous ligand, a polypeptide, a cyclic peptide, an antibody, a protein, and the like, which are considered to have an agonist activity). In examples of the specific procedure, a reporter gene capable of visualizing a change of the intracellular signaling molecule associated with activation of the target cell membrane protein is transfected in advance into the first cell expressing the target cell membrane protein. Then, when the target substance binds to the target cell membrane protein, the change in the expression of the reporter gene can be visualized. As a result, the binding between the cell membrane protein and the target substance can be indirectly visualized. For example, it can be indirectly visualized by using Promega's pGL4 Signaling Vector series and luciferin as a luminescent substrate. Then, a positive microwell can be identified by using a luminescent microscope or an instrument including the luminescent microscope.

Another example that can be applied for the indirect technique is visualization of a change of cAMP in a cell. For example, the change of the amount of cAMP in a cell can be visualized by detecting the specific phosphorylation of CREB (cAMP response element binding protein) observed when a substance that activates cell membrane proteins is added with anti-phosphorylated antibodies and fluorescence-labeled secondary antibodies. Yet another example includes visualization of changes in Ca in a cell. The change of Ca in a cell can be indirectly visualized by a change of the fluorescence intensity of the intracellular fluorescent Ca indicator.

When the first cell is labeled with fluorescence in advance before addition of the label substance, positive microwells can be identified more easily and quickly. For example, an antibody labeled with a fluorescent substance (first fluorescent substance) is employed as the label substance, and the first cell is labeled with another fluorescent substance (second fluorescent substance). Herein, as the second fluorescent substance, a fluorescence substance that emits fluorescence having a different fluorescence wavelength from that of the fluorescence emitted by the first fluorescent substance is employed. In other words, the fluorescence wavelength of the fluorescence emitted by the first fluorescent substance is different from the fluorescence wavelength of the fluorescence emitted by the second fluorescent substance. For example, as the secondary fluorescent substance, Calcein-AM, Fluorescein diacetate (FDA). Carboxyfluorescein diacetate (CFDA), CytoRed, Propidium iodide (PI). Ethidium bromide (EB), Acridine orange (AO), DAPI, Hoechst 33342, or Hoechst 33258 is used. On the other hand, Alexa Fluor 488 is used as the first fluorescent substance. Thereby, the first cell to which the labeled antibody binds and the first cell to which the labeled antibody does not bind can be easily distinguished from each other by the difference of the fluorescence emitted. Then, positive microwells can be identified using a fluorescence microscope or an instrument including a fluorescence microscope.

Antibodies are usually secreted extracellularly, but it is known that there are membrane-type antibodies that are not secreted extracellularly. Therefore, non-secreted membrane-type antibodies may be present on the surface of the second cell. In this case, when the labeled anti-IgG antibody is added, it may bind not only to the antibody binding to the first cell but also to the membrane-type antibody on the second cell. However, according to the above embodiment using the first fluorescent substance and the second fluorescent substance, only the antibody binding to the first cell can be specifically detected.

In the visualization step, after the label substance is added, it is preferable to perform a washing step in order to remove excess label substances. The washing is not particularly limited as long as it is performed under the conditions that the first cell and the second cell are retained in the microwell (the condition that the first cell and the second cell do not flow away). Examples of the washing include gently washing a microwell several times with a phosphate buffer, HBSS, or cell culture medium. When the washing step is included, even when the expression level of the target cell membrane protein on the cell membrane of the first cell is very low, the signal including the target substance that binds to the target cell membrane protein can be detected with high sensitivity.

<Recovery of Second Cell>

After identifying the positive microwell, the second cell is recovered as a target cell. Recovery of the second cell from the microwell can be performed, for example, using a micromanipulator. For example, a capillary having a diameter of a few pin to 50 pin is inserted into the positive microwells and the second cell can be recovered as it is alive. The operation by the micromanipulator may be performed automatically or manually. For example. Cell Picking System (AS ONE Corporation) and Cell Celector (Automated Lab Solution) can be used for recovery.

The recovered second cell is preferably recovered in a suitable cell culture medium or in a cell lysis solution (Lysis buffer) for rapid extraction without degrading mRNA.

Note here that when two second cells have been introduced into the positive microwell, for example, the two second cells are recovered into a cell culture medium, then both are separated from each other, and one of them may be used as the target cell. Alternatively, two second cells are recovered in Lysis buffer, nucleic acid encoding two kinds of target substances is obtained and isolated by the method described below, and one of the nucleic acids can be used as the target nucleic acid (target gene).

<Method for Producing Nucleic Acid, Recombinant Cell, and Specific Binding Substance>

The present invention includes a method for producing a nucleic acid. The method includes obtaining a nucleic acid (gene) encoding a target substance from a target cell selected from the population of second cells by the method mentioned above. The present invention also includes a method for producing a recombinant cell. The method includes transfecting the nucleic acid into a host cell to obtain a recombinant cell expressing the target substance. Furthermore, the present invention includes a method for producing a target substance by culturing the recombinant cell and obtaining the target substance from the cultured product. Preferably, the target substance is an antibody.

As a method for obtaining a nucleic acid encoding a target substance from a second cell, a well-known method can be used. For example, cDNA is synthesized by combining reverse transcription reaction and a PCR method. Then, the nucleic acid of interest can be isolated from the cDNA.

As a method for obtaining a recombinant cell expressing the target substance, a well-known method can be used. For example, the isolated nucleic acid of interest is incorporated into an appropriate vector. This vector can be transfected into a host cell such as *Escherichia coli*, yeast, and mammalian cells (for example, a CHO cell, an HEK293 cell, or an NS0 cell) to obtain the recombinant cell of interest.

Then, the recombinant cell is cultured, and the target substance can be obtained from the cultured product (for example, culture supernatant).

The case where the target substance is an antibody will be further described. Isolation of the antibody gene from the second cell can be performed by, for example a combination of the methods described in WO2009/091048, WO2009/110606, and WO 2011/027808, or the method (MAGrahd method) described in Nobuyuki Kurosawa, Megumi Yoshioka, Rika Fujimoto, Fuminori Yamagishi and Masaharu Isobe, "Rapid production of antigen-specific monoclonal antibodies from a variety of animals", BMC Biology, 10:80, 2012.

Recombinant cells expressing a complete antibody, a functional antibody fragment, a single chain antibody, or a multispecific antibody can be constructed by modifying the isolated antibody gene. Similarly, recombinant cells expressing complete human antibodies, humanized antibodies, or chimeric antibodies can be constructed. Similarly, recombinant cells expressing a felinized antibody or a caninized antibody can be constructed.

When the second cell itself can be stably cultured, the second cell itself is cultured and a target substance such as an antibody can be obtained from the cultured product. In other words, the present invention includes a method for producing a target substance by culturing a target cell selected from a population of second cells by the method mentioned above and obtaining the target substance from the cultured product.

As a method for purifying a target substance such as an antibody from a cultured product, a well-known method can be used. For example, various chromatography such as affinity, ion exchange, and gel filtration chromatography can be employed. Examples of ligands in the affinity chromatography include protein A, protein G, anti-FLAG antibody, anti-V5 antibody, and the like.

<Method for Producing Pharmaceutical Composition>

The present invention includes a method for producing a pharmaceutical composition. The method includes combining the nucleic acid produced by the above method with a pharmaceutically acceptable carrier or additive to obtain a pharmaceutical composition containing the nucleic acid as an active ingredient. Furthermore, the present invention includes a method for producing a pharmaceutical composition by combining the target substance produced by the above method with a pharmaceutically acceptable carrier or additive to obtain a pharmaceutical composition containing the target substance as an active ingredient.

The target substance produced by the present invention, for example, an antibody, is useful as an active ingredient of a pharmaceutical composition (therapeutic agent). The pharmaceutical composition can contain a target substance such as an antibody produced by the present invention, and a pharmaceutically acceptable carrier or additive. Preferably, the pharmaceutical composition blocks or activates intracellular signal transduction mechanism specific to a target cell membrane protein.

The pharmaceutical composition can be administered systemically or topically, in an oral route or a parenteral route. Examples of a dosage form include an injection form, a nasal dosage form, a pulmonary dosage form, a transdermal dosage form, and the like. In the case of an injection form, it may be systemically or topically administered, for example, by intravenous injection, intramuscular injection, intraperitoneal injection, subcutaneous injection or the like. The administration method may be appropriately selected depending on the age and the symptom of a patient. When the target substance is an antibody, for example, the dosage of the antibody may be selected within the range of 0.0001 mg to 1000 mg per 1 kg of body weight per one dosage. Alternatively, for example, the dose may be selected so that the amount of the antibody is within the range of 0.001 to 100000 mg/body per a patient. However, the dose of the antibody is not limited to these ranges.

The pharmaceutical composition can be formulated according to an ordinary method (for example, Remington's Pharmaceutical Science, latest edition, Mark Publishing Company, Easton, U.S.A). Examples of the agent or the additive include surfactants (PEG, Tween, and the like), excipients, antioxidants (ascorbic acid and the like), coloring agents, flavoring agents, preservatives, stabilizers, buffers (phosphoric acid, citric acid, other organic acid, and the like), chelators (EDTA, and the like), suspending agents, tonicity agents, binders, disintegrating agents, lubricants, fluidic accelerating agents, and flavoring substances, and the like. Specific examples thereof may include light anhydrous silicic acid, lactose, crystalline cellulose, mannitol, starch, carmellose calcium, carmellose sodium, hydroxypropyl cellulose, hydroxypropylmethyl cellulose, polyvinylacetaldiethylamino acetate, polyvinylpyrrolidone, gelatin, medium-chain triglyceride, polyoxyethylene hardened castor oil 60, sucrose, carboxymethylcellulose, cornstarch, inorganic salts, and the like. Examples of the agent or the additive also include other low molecular-weight polypeptides; proteins such as serum albumin, gelatin, and immunoglobulin; and amino acid such as glycine, glutamine, asparagine, arginine, and lysine.

When the pharmaceutical composition is an aqueous solution for injection, for example, saline, an isotonic solution including glucose or other adjuvants, for example, D-sorbitol, D-mannose, D-mannitol, and sodium chloride are used, and an appropriate solubilizing agent, for example, alcohol (ethanol and the like), polyalcohol (propyleneglycol, PEG, and the like), a nonionic surfactant (polysorbate 80, HCO-50), and the like, may be used together. An antibody as an active ingredient may be encapsulated in a microcapsule (for example, microcapsule of hydroxymethyl cellulose, gelatin, poly(methyl methacrylate)), or formulated as a colloid drug delivery system (for example, liposome, albumin microsphere, microemulsion, nanoparticle, and nanocapsule) as is necessary (see "Remingto's Pharmaceutical Science 16th edition", Oslo Ed. (1980) or the like).

Furthermore, a technique for improving a therapeutic effect by directly fusing other drugs into the antibody, and such a technique is applicable to the pharmaceutical composition of the present invention, is known.

It is also conceivable to incorporate a nucleic acid (gene) obtained in the present invention, for example, an antibody gene into a vector for a gene therapy, and to prepare a gene therapeutic agent. Examples of an administration method of the gene therapeutic agent (recombinant vector) include, besides direct administration by a naked plasmid, a method of packaging it in liposome or the like for administration, a method of incorporating it into various viral vectors such as retroviral vector, adenoviral vector, vaccinia virus vector, poxvirus vector, adeno-associated virus vector, or HVJ vector for administration (see, Adolph "Viral Genomic Methods", CRC Press, Florid (1996)), and a method of coating a bead carrier such as a colloidal gold particle (WO 93/177006).

In other words, the gene therapeutic agent may be administered in any method as far as the antibody as the active ingredient is expressed in a living body, and is able to exert its action. Preferably, a sufficient amount can be administered by an appropriate parenteral pathway. Examples of the administration by parenteral routes include injection or infusion via intravenous, intraperitoneal, subcutaneous, intradermal, intra-adipose tissue, intra-mammary gland tissue, inhalation or intramuscular route, or a gas-induced particle bombardment method (by an electron gun or the like), a method via a mucosal route such as a nasal formulation, and the like. Furthermore, the gene therapeutic agent may be administered to a cell by ex vivo liposome transfection, a particle bombardment method (U.S. Pat. No. 4,945,050), or by viral infection, and reintroducing the cell into the animal.

<Reagent for Detecting Cell Membrane Protein>

The present invention includes a reagent for detecting desired cell membrane protein, including the target substance produced by the method mentioned above. For example, a reagent including an antibody (target substance) produced by the method of the present invention is used to bring the antibody into contact with blood cells derived from humans or non-human mammals. Furthermore, a label substance including a fluorescent substance or a coloring agent is brought into direct or indirect contact therewith. Then, expression of the desired cell membrane protein can be detected by flow cytometry or a plate reader. Furthermore, by using the reagent, the antibody can be brought into contact with a pathological tissue piece derived from a human or a non-human mammal to detect the expression of a desired cell membrane protein.

Furthermore, a kit for detecting cell membrane proteins including the above-mentioned reagent can be constructed. For example, a kit for detecting a cell membrane protein can be constructed by combining the above reagent with a label substance, or the like.

The present invention includes a method for detecting the desired cell membrane protein using the target substance produced by the above-mentioned method. The present invention includes use of the target substance produced by the above-mentioned method for detecting the desired cell membrane protein.

In following Examples 1 to 8, cells producing a specific binding antibody against an Apelin receptor (hereinafter, also abbreviated as APLNR), which is one of human GPCRs, were mainly selected. Furthermore, the antibody gene was isolated from the selected cells, and recombinant cells expressing the antibody were constructed. Furthermore, the functionality of the antibody expressed by the recombinant cell was evaluated.

Example 1

(1-1) Preparation of APLNR Expression Vector

An artificially synthesized gene (SEQ ID NO: 1) including a human APLNR gene sequence (NM_005161.4) registered in Genebank and optimized for the codon of mouse amino acid was prepared. A vector pCI-APLNR-GroEL including a fusion gene of a human APLNR gene and a GroEL gene was constructed using this artificially synthesized gene according to the method described in WO 2012/043533 (Japanese Patent No. 5315495).

(1-2) Preparation of APLNR Stable Expression Cell (First Cell)

The artificial synthetic gene (SEQ ID NO: 1) was transfected into a pEFS/FRT/V5-DEST vector (Invitrogen) to construct pEF-FRT-APLNR. In human APLNR expressed from pEF-FRT-APLNR, V5 and 6×HIS tags are added to the C-terminal.

Flp-In-CHO cells (Invitrogen) were cultured in a Ham's F-12 medium (Invitrogen) including 10% fetal bovine serum, 100 units/mL penicillin, and 100 µg/mL streptomycin. Into the cells, pEF-FRT-APLNR and pOG44 plasmid (Invitrogen) were simultaneously transfected using Lipofectamin 2000. From the next day of the transfection, the medium was replaced with a Ham's F-12 medium including 500 µg/mL hygromycin (Invitrogen), and the cells were cultured for two weeks while the medium was changed every three days. Hygromycin-resistant cells were cloned from the formed colonies by the limiting dilution method.

A phycoerythrin (PE)-labeled anti-mouse IgG antibody (Beckman Coulter) was used as a secondary antibody, binding of the obtained hygromycin-resistant cells and anti-Apelin antibody (R&D) or anti-V5 tag antibody (Invitrogen) was analyzed with a flow cytometer. As a result, it was demonstrated that the obtained hygromycin-resistant cells showed PE-positive and stably expressed human APLNR. Hereinafter, this cell will be referred to as a human APLNR stable expression CHO cell line (first cell).

Example 2

(2-1) Obtaining of Immunized Animal by DNA Immunization Method

Vector pCI-APLNR-GroEL was injected into 8-week-old mouse ICR (female) according to the method described in WO 2012/043533 (Japanese Patent No. 5315495) in multiple doses (DNA immunization).

(2-2) Preparation of Cell Population (Second Cells) Including Antibody-Producing Cell from Spleen The spleen was extirpated from the mouse that had been subjected to DNA-immunization in (2-1) and recovered in a 6-well plate including refrigerated HBSS. After removing the attached connective tissue and adipose tissue, the spleen was loosened and lymphocytes were released in a new HBSS. Cells were recovered and resuspended in 10 ml. HBSS. The unruptured tissue was separated with a cell strainer, and then the tissue was centrifuged at 2000 rpm for five minutes to recover cells. The recovered cells were suspended in 1 mL of hemolytic solution, and incubated at 37° C. for five minutes to remove red blood cells. Lymphocyte cells were recovered by centrifugation at 10 rpm for five minutes.

The cell population of about $1.3 \times 10^5$ cells (second cells) including candidates for desired antibody-producing cells (target cells) was isolated from $2.5 \times 10^7$ lymphocyte cells mentioned above using the EasySep Mouse Biotin Positive Selection Kit (STEMCELL TECHNOLOGIES).

Example 3

(3-1) Preparation of Hybridoma Cells (Second Cells)

Myeloma cells (SP2/0) used for cell fusion were initiated five days before the cell fusion, subcultured once two days before the cell fusion, and then used.

Frozen spleen cells of the immunized mice obtained in Example 2 were thawed and suspended in a RPM11640 medium (containing 10% FBS) at 37° C. Then, the number of cells was counted. Spleen cells and myeloma cells (SP210) were mixed with each other such that a cell number ratio was 1:1. Note here that the myeloma cells were initiated five days before the cell fusion, subcultured once two days before the cell fusion, and then used. The cell mixture was centrifuged, and then the cells were washed with an ECF buffer. Similar washing was performed further twice.

The cell fusion of splenic cells and myeloma cells was performed using the cell fusion device ECFG21 (Nepa Gene Co., Ltd.). After the cell fusion, RPMI1640 medium (containing FBS without antibiotics) of the cell solution was added at 2 times the amount of the cell solution and allowed to stand in a $CO_2$ incubator for one hour. The cells were recovered by centrifugation and suspended in HAT medium (RPM11640 with 10% FBS, 2-mercaptomethanol (×500). HFCS (×100), HAT (×50)). Using 96-well plate, 24-well plate, and 10 cm dish, antibody-producing hybridoma cells were cloned and cultured according to an ordinary method.

Example 4

(4-1) Selection of Specific Antibody-Producing Hybridoma Using Microwell

Microwell chamber ASMC30-20P (AS ONE Corporation) was prepared. This microwell chamber is a substrate in which 84,640 microwells each having a diameter of 30 µm are arranged at equal intervals in an area of about 1.5 cm×about 2.4 cm. The depth of each microwell is equal to the diameter of each microwell. The pitch between the microwells is twice the diameter of each microwell. In the conventional technologies, it is common to be used in a state in which one cell is accommodated in a microwell. However, in this Example, the experiment was performed by accommodating the first cell and the second cell, that is, two or more cells in the microchamber. The description follows.

Human APLNR stable expression CHO cells (first cells) were suspended in an F-12 medium (containing 10% FBS, Penicillin/Streptomycin) to prepare a cell suspension at $3 \times 10^5$ cells/500 µL. This cell suspension was filled in each microwell. The microchamber was centrifuged at 300 rpm for two minutes twice to prepare one or two first cells accommodated in each microwell. After the microchamber was washed with F-12 medium, 500 µL of F-12 medium was added. Incubation was performed in a $CO_2$ incubator at 37° C. for one hour, and the first cells were allowed to adhere to the bottom surface of the microwell while the functionality as the first cell was maintained. A CytoRed solution that had been adjusted at the concentration of 10 nM with an F-12 medium was added, and further incubation was performed at 37° C. for one hour to stain the first cells. Washing with F-12 medium three times to remove excess CytoRed, and then 1 mL of F-12 medium was filled in the microchamber.

A population of hybridomas (second cells) prepared in Example 3 were cultured to prepare a cell suspension at $3 \times 10^5$ cells/50) µL. This cell suspension was filled in each microwell. The microchamber was centrifuged twice at 300 rpm for two minutes to prepare one or two second cells in each microwell. After the microchamber was washed with a medium, an appropriate amount of medium was added, followed by incubation at 37° C. for 30 minutes to secrete antibodies from the hybridoma. After the microwells were washed to remove a supernatant. Alexa Fluor 488-labeled anti-mouse IgG antibody (secondary antibody; label substance) diluted 500-fold with RPM11640 (containing 10% FBS) was applied, and incubation was performed at 37° C. for 30 minutes. After washing with RPMI1640 (free of phenol red, and containing 1% FBS) three times, 1 mL of RPMI1640 was added. The microchamber was set in a cell picking system (AS ONE Corporation), and signal on transmitted light images of all microwells and two types of fluorescence images was acquired. Fluorescence detection of CytoRed was performed under the conditions of an excitation wavelength of 543 nm and an emission wavelength of 593 nm. Fluorescence detection of Alexa Fluor 488 was performed under the conditions of an excitation wavelength of 482 nm and an emission wavelength of 536 nm.

Figure 2:
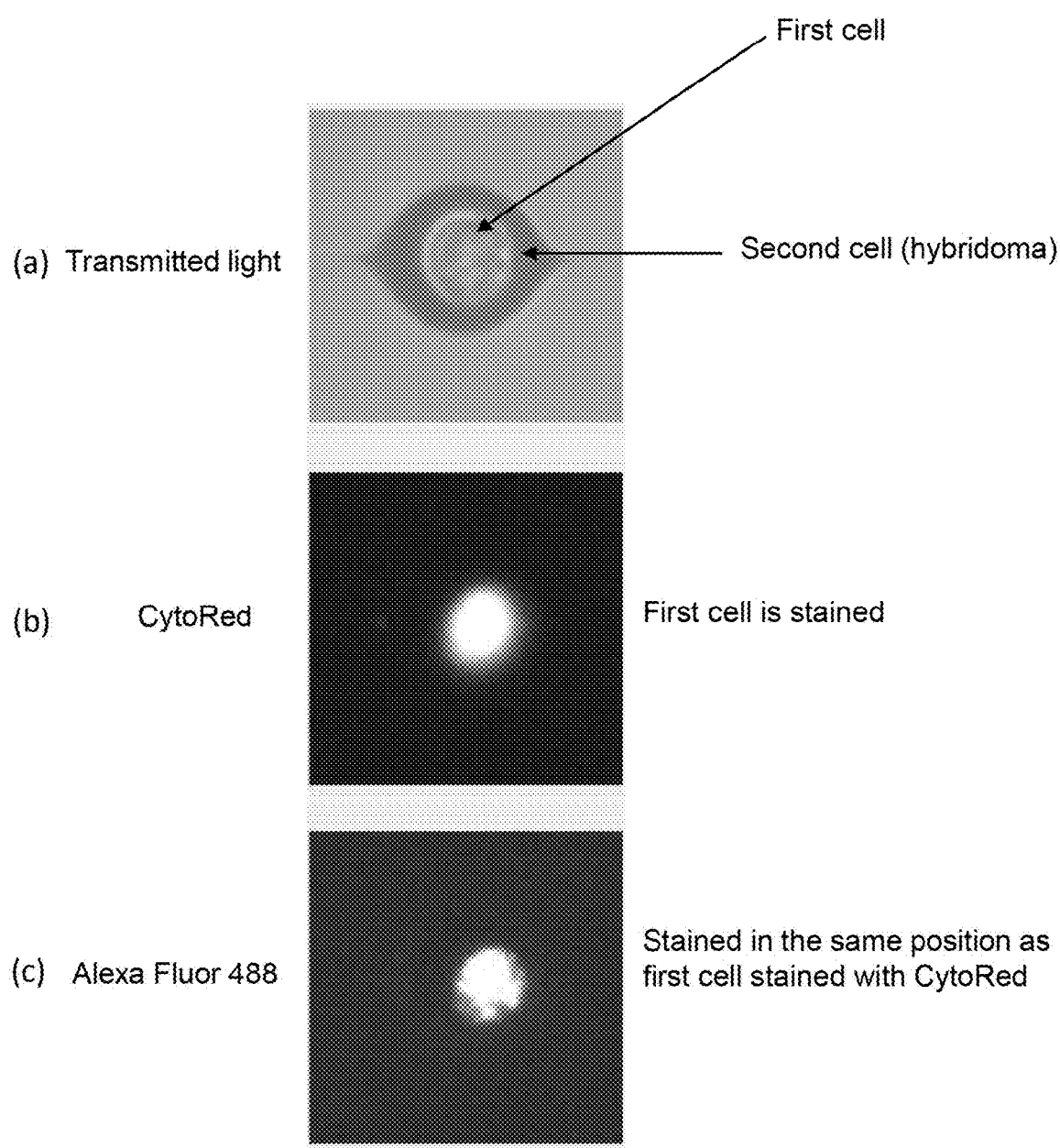
FIG. 2 is a photograph showing an example of an image of a positive microwell in Example 4, wherein (a) shows an observation result of transmitted light, (b) shows that of CytoRed-derived fluorescence, and (c) shows that of Alexa Fluor 488-derived fluorescence.
Figure 3:
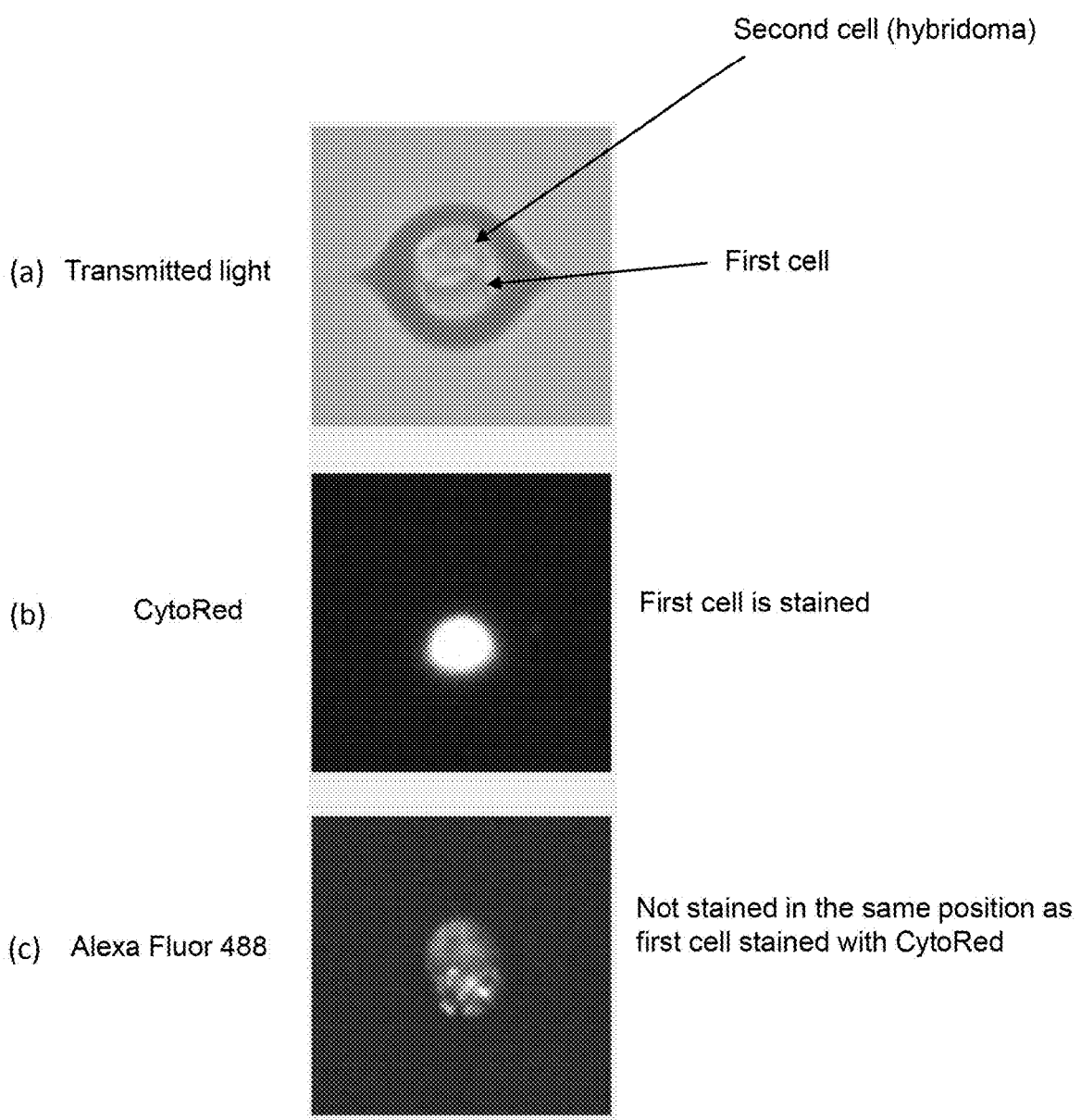
FIG. 3 is a photograph showing an example of an image of a negative microwell in Example 4, wherein (a) shows an observation result of transmitted light, (b) shows that of CytoRed-derived fluorescence, and (c) shows that of Alexa Fluor 488-derived fluorescence.

FIGS. 2(a) to (c) each shows an example of an image of a hybridoma producing an antibody that specifically binds to APLNR on the surface of the first cell, that is, an image of a positive microwell in which a target cell is determined to be accommodated. On the other hand, FIGS. 3(a) to (c) each shows an example of an image of a hybridoma producing an antibody that does not specifically bind to APLNR on the surface of the first cell, that is, an image of a negative microwell in which a not-target cell is determined to be accommodated. In FIGS. 2 and 3, (a) shows an observation result of transmitted light, (b) shows that of CytoRed-derived fluorescence, and (c) shows that of Alexa Fluor 488-derived fluorescence.

As shown in FIG. 2(c), in the microwell in which the target cell and the APLNR-expressing CHO cell coexisted, fluorescence of Alexa Fluor 488 was observed in the same position as the CHO cell labeled with CytoRed. In other words, the CHO cell coexisting with the target cell in the microwell was co-stained with Alexa Fluor 488 and CytoRed. Thus, it was observed that Alexa Fluor 488-labeled anti-IgG antibody bound to the surface of CHO cell.

On the other hand, as shown in FIG. 3(c), in the microwell where undesired target cell and the APLNR-expressing CHO cell coexisted, fluorescence of Alexa Fluor 488 was not observed in the same position as the CHO cell labeled with CytoRed. In other words, the Alexa Fluor 488-labeled anti-IgG antibody did not bind to the surface of CHO cell, and the CHO cell was not co-stained with Alexa Fluor 488 and CytoRed. Thus, it was observed that the Alexa Fluor 488-labeled anti-IgG antibody did not bind to the surface of CHO cell.

Finally, 16 positive microwells including the target cell were identified from 84.640 microwells.

Among the positive microwells, microwells each containing only one hybridoma were selected. From the selected microwells, hybridomas were aspirated using a capillary having a diameter of several µm to several tens of µm and recovered into a cell lysis solution. Finally, at least three independent hybridomas were selected.

According to the method of this Example, the selection of hybridomas, which normally takes about 60 days, was able to be completed within 7 days.

Example 5

(5-1) Isolation of Antibody Gene from Selected Hybridomas

From one of the hybridomas selected in Example 4, an antibody gene was obtained by the MAGrahd method (Nobuyuki Kurosawa, Megumi Yoshioka, Rika Fujimoto. Fuminori Yamagishi and Masaharu Isobe, "Rapid production of antigen-specific monoclonal antibodies from a variety of animals". BMC Biology, 10:80, 2012). Specifically, 5 µL of the cell lysis solution obtained in Example 4 and 5 µg of oligo dT magnet were mixed, and cell-derived mRNA was captured on the oligo dT magnet. The oligo dT magnet was washed with a washing solution using a MAGrahd reactor tray and a neodymium magnet, and then cDNA synthesis was performed by a reverse transcription reaction. Furthermore, after the magnet was washed, a 5' terminal translational reaction was performed. The gene of the antibody heavy chain variable region (VH region) and the gene of the antibody light chain variable region (VL region) were isolated and amplified by the 5' race PCR method using the synthesized cDNA mentioned above.

Note here that the PCR was performed twice in order to increase the specificity of the amplified product. In the first PCR, a first forward primer (SEQ ID NO: 3) that amplifies the VH region and the VL region in common, a first reverse primer (SEQ ID NO: 4) that specifically amplifies the VH region, and a second reverse primer (SEQ ID NO: 5) that specifically amplifies the VL region are mixed and used. In the second PCR, the first amplified product was used as a template, the second forward primer (SEQ ID NO: 6) and the third reverse primer (SEQ ID NO: 7) that specifically amplifies the VH region were used as primers for amplification of the VH region, and the second forward primer (SEQ ID NO: 6) and a fourth reverse primer (SEQ ID NO: 8) that specifically amplifies the VL region were used as primers for amplification of the VH region.

When the sample after the second PCR was subjected to agarose gel electrophoresis, corresponding amplified products were confirmed in the VH region at the position of 750 bp and in the VL region at the position of 550 bp, respectively.

(5-2) Construction of Antibody Expression Unit

An antibody expression unit was constructed by a TS-jPCR method (Megumi Yoshioka. Nobuyuki Kurosawa and Masaharu Isobe. "Target-selective joint polymerase chain reaction: A robust and rapid method for high-throughput production of recombinant monoclonal antibodies from single cells", BMC Biotechnol. 2011 Jul. 21; 11:75). Specifically, a gene in the VH region amplified in (5-1), a gene in the antibody heavy chain constant region, and a promoter region required for gene expression were fused using PCR to construct an antibody expression unit expressing a full-length antibody heavy chain. Similarly, a gene in the VL region amplified in (5-1), a gene in the antibody light chain constant region, and a promoter region required for gene expression were fused by PCR to construct an antibody expression unit expressing a full-length antibody light chain. By co-transfecting these antibody expression units into mammalian cells, a recombinant cell that transiently expresses the desired antibody (IgG) can be obtained.

(5-3) Transfection of Antibody Expression Unit into Mammalian Cell

The above two kinds of antibody expression units were co-transfected into HEK293FT cell by the method described in the above document (Nobuyuki Kurosawa et al., BMC Biology, 10:80, 2012). Specifically, the HEK293FT cells were seeded in the collagen-coated 96-well plate at $1.5 \times 10^4$ cells/100 μL/well. The two kinds of antibody expression units constructed in (5-2) were co-transfected into the HEK293FT cells using Lipofectamine 2000. Cell supernatants were recovered on Day 3 after the transduction and used for binding evaluation of the expressed antibody.

As Comparative Examples, the cell supernatant was recovered using an unintended hybridoma recovered from the negative microwell by the same procedures as in (5-1) to (5-3).

(5-4) Binding Assay of APLNR and Antibody Using Flow Cytometry

A human APLNR stable expression CHO cell line was cultured in a dish having a diameter of 10 cm. The cells were washed with PBS three times, 1 mL of cell detachment buffer was added, and the obtained product was incubated at 37° C. for 15 minutes. Detached cells were suspended in an FACS buffer, and the suspension was centrifuged for five minutes at 1000 rpm, and resuspended in the FACS buffer such that the cell concentration became $1 \times 10^7$ cells/mL. Fc Block (Becton Dickinson) was added in an amount of 1/500 of the cell suspension, and subjected to blocking at 4° C. for 30 minutes. After blocking, the cells were suspended such that the cell concentration became $2 \times 10^5$ cells/50 μL. In a 96-well plate, the cell suspension and the cell supernatant recovered in (5-3) were mixed with each other and incubated at 4° C. for one hour. After incubation, the cells were washed with 100 μL FACS buffer twice. A diluted solution of a fluorescence-labeled anti-IgG antibody (secondary antibody) was added to each well in an amount of 50 μL, and the mixture was incubated at 4° C. for one hour, and a secondary antibody was allowed to bind to the antibody that bound to the CHO cell surface. The cells were washed with 100 μL FACS buffer twice, and then the cells were suspended in 80 μL FACS buffer. Then, the fluorescence intensity of the cell surface was measured by a flow cytometry method.

Figure 4:
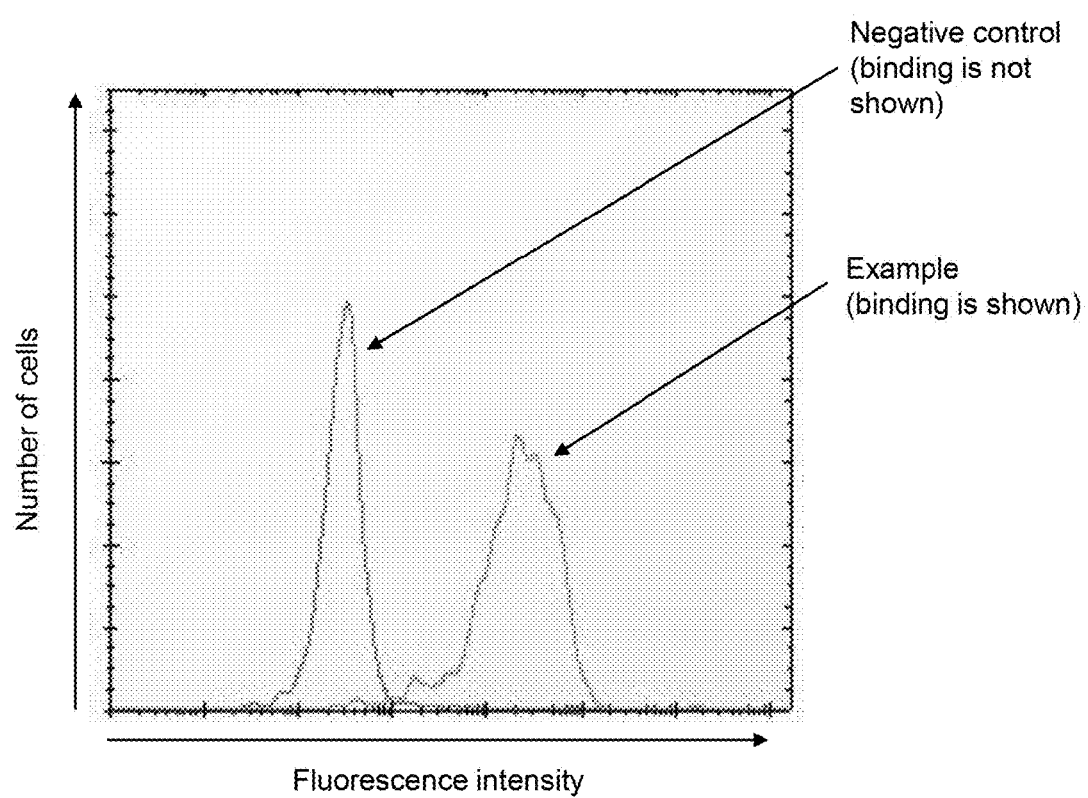
FIG. 4 is a view showing a result of a flow cytometry of a genetically recombinant antibody derived from hybridoma recovered from a positive microwell in Example 5.

FIG. 4 shows the results of the flow cytometry. The antibody expressed by the recombinant cells obtained in (5-3) showed binding to a human APLNR-expressing CHO cell. Note here that the antibody did not show binding to a wild-type CHO cell that did not express APLNR.

Figure 5:
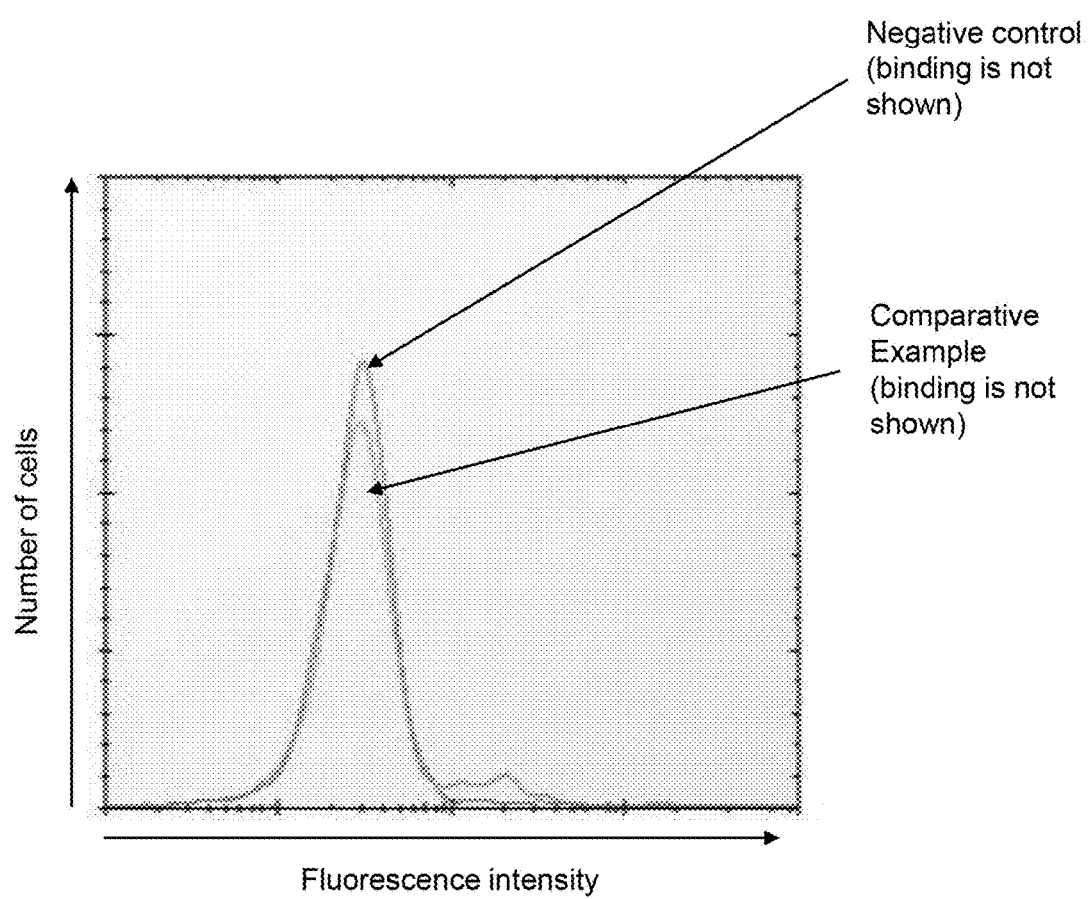
FIG. 5 is a view showing a result of a flow cytometry of a genetically recombinant antibody derived from hybridoma recovered from a negative microwell in Example 5.

On the other hand, as shown in FIG. 5, in Comparative Example using an undesired target hybridoma recovered from negative microwells, the antibody expressed by the recombinant cell did not show binding to the human APLNR stable expression CHO cell.

From the above, it was shown that the antibody obtained by this Example had specific binding to the human APLNR-expressing CHO cells.

Example 6

(6-1) Selection of Specific Antibody-Producing Lymphocyte Cells Using Microwells A cell producing an antibody of interest was selected from a population of non-immortalized lymphocyte cells (second cells) prepared in Example 2 according to the method of Example 4. The description follows.

In the same manner as in Example 4, a human APLNR stable expression CHO cell (first cell) is allowed to adhere to the bottom surface of the microwell. Furthermore, the first cell was stained with CytoRed, and 1 mL of F-12 medium was filled into the microchamber.

A population of lymphocytes (second cells) prepared in Example 2 was suspended in RPMI1640 to prepare a cell suspension at $3 \times 10^5$ cells/500 μL. This cell suspension was filled in each microwell. The microchamber was centrifuged at 300 rpm for two minutes twice to prepare one or two second cells accommodated in each microwell. After the microchamber was washed with RPMI1640, 1 mL of RPMI1640 was added, followed by incubation at 37° C. for 30 minutes to promote antibody production from lymphocytes. The microwell was washed to remove a supernatant, Alexa Fluor 488-labeled anti-mouse IgG antibody (secondary antibody; label substance) diluted 500-fold with RPMI1640 (containing 10% FBS) was applied, and then, incubation was performed at 37° C. for 30 minutes. After washing with RPM11640 (free of phenol red, and containing 1% FBS) three times, 1 mL of RPM11640 was added. The microchamber was set in a cell picking system (AS ONE Corporation), and signals on transmitted light images of all microwells and two types of fluorescence images were obtained.

Figure 6:
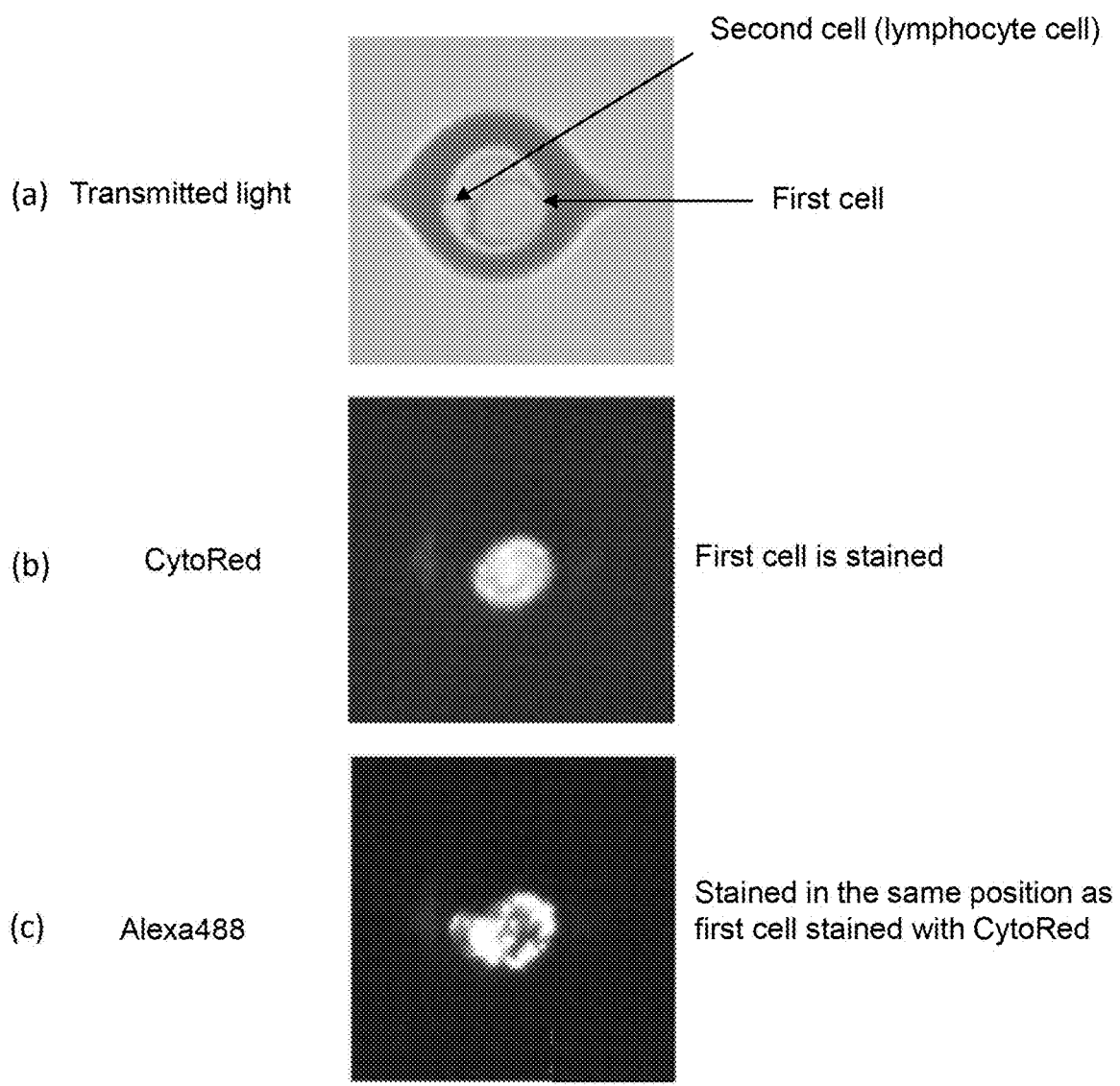
FIG. 6 is a photograph showing an example of an image of a positive microwell in Example 6, wherein (a) shows an observation result of transmitted light, (b) shows that of CytoRed-derived fluorescence, and (c) shows that of Alexa Fluor 488-derived fluorescence.
Figure 7:
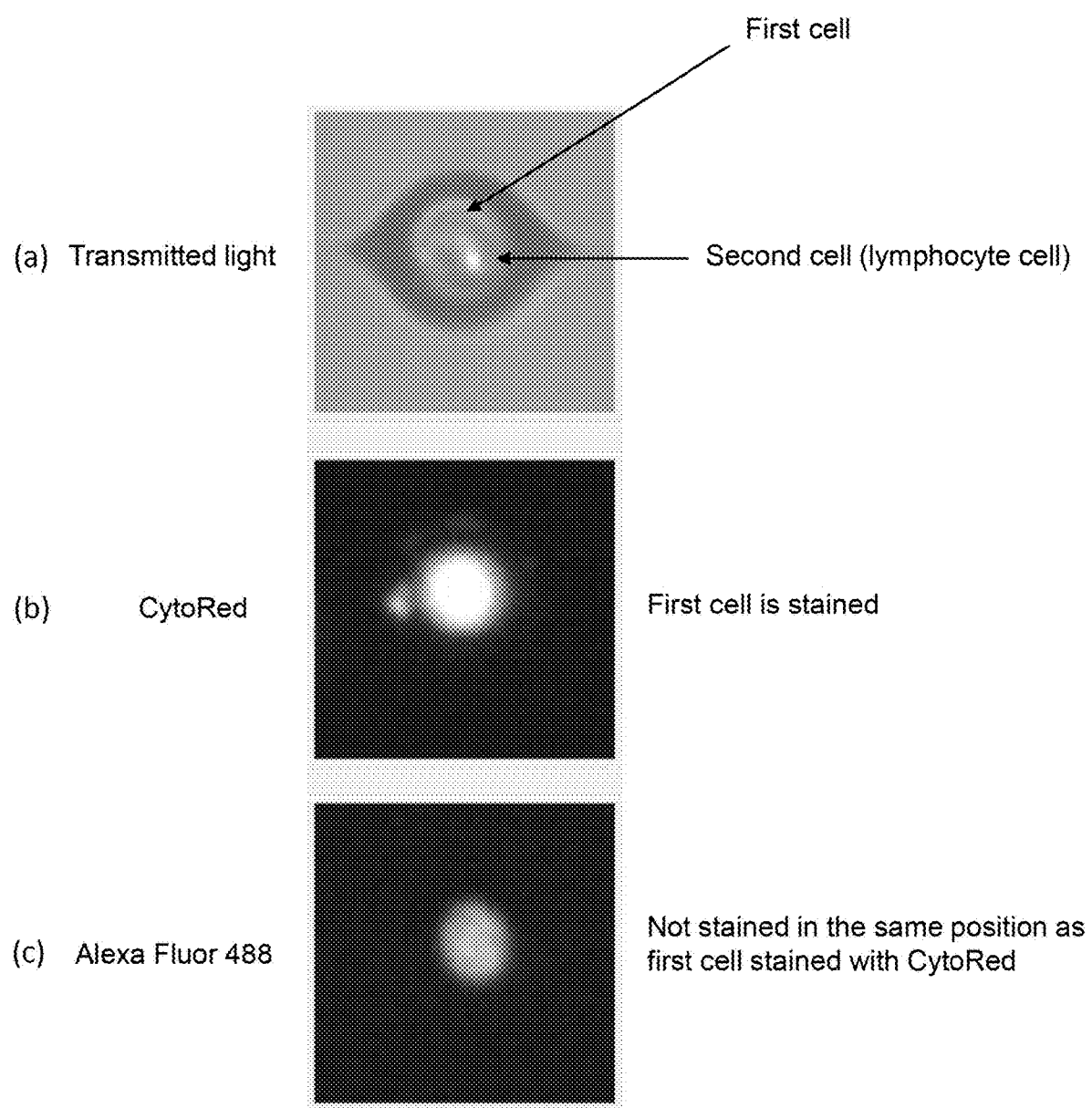
FIG. 7 is a photograph showing an example of an image of a negative microwell in Example 6, wherein (a) shows an observation result of transmitted light, (b) shows that of CytoRed-derived fluorescence, and (c) shows that of Alexa Fluor 488-derived fluorescence.

FIG. 6(a) to (c) each shows an example of an image of a lymphocyte producing an antibody that specifically binds to APLNR on the surface of the first cell, that is, an image of a positive microwell in which a target cell is determined to be accommodated. On the other hand, FIGS. 7(a) to (c) each shows an example of an image of a lymphocyte producing an antibody that does not specifically bind to APLNR on the surface of the first cell, that is, an image of a negative microwell in which an undesired-target cell is determined to be accommodated. In FIGS. 6 and 7, (a) shows an observation result of transmitted light, (b) shows that of CytoRed-derived fluorescence, and (c) shows that of Alexa Fluor 488-derived fluorescence.

As shown in FIG. 6(c), in the microwell in which the target cell and the APLNR-expressing CHO cell coexisted, fluorescence of Alexa Fluor 488 was observed in the same position as the CHO cell labeled with CytoRed. In other words, the CHO cell coexisting with the target cell in the microwell was co-stained with Alexa Fluor 488 and CytoRed. In particular, fluorescence of Alexa Fluor 488 was strongly observed near the target cells (lymphocytes). Thus, it was observed that Alexa Fluor 488-labeled anti-IgG antibody bound to the surface of CHO cell.

On the other hand, as shown in FIG. 7(c), in the microwell where not-target cell and the APLNR-expressing CHO cell coexisted, fluorescence of Alexa Fluor 488 was not observed in the same position as the CHO cell labeled with CytoRed, but only observed from the cell membrane surface of lymphocytes. In other words, the Alexa Fluor 488-labeled anti-IgG antibody did not bind to the surface of CHO cell, and the CHO cell was not co-stained with Alexa Fluor 488 and CytoRed. Thus, it was observed that the Alexa Fluor 488-labeled anti-IgG antibody did not bind to the surface of CHO cell.

Finally, 40 positive microwells including target cells were identified from 84,640 microwells.

Among the positive microwells, microwells each including only one lymphocyte were selected. From the selected microwells, lymphocytes were aspirated using a capillary having a diameter of several μm to several tens of μm and recovered in a cell lysis solution. Finally, at least 14 independent antibody-producing lymphocytes, in which binding to the target substance was confirmed by flow cytometry, were selected.

According to the method of this example, the selection of desired lymphocytes directly from the lymphatic tissue was able to be completed in only one day without through the conventional hybridoma method that has taken about 60 days.

Example 7

(7-1) Isolation of Antibody Gene from Selected Lymphocytes

An antibody gene was obtained from one of the lymphocytes selected in Example 6 by the same procedure as in Example 5.

(7-2) Construction of Antibody Expression Unit

Two types of antibodies expression units expressing a full-length antibody heavy chain and a full-length antibody light chain from the antibody gene obtained in (7-1) were constructed by the same procedure as in Example 5.

(7-3) Transfection of Antibody Expression Unit into Mammalian Cells

The antibody expression units obtained in (7-2) were co-transfected into an HEK293FT cell by the same procedure as in Example 5. A cell supernatant was recovered 48 hours after the transfection and used for evaluating the functionality of the expressed antibody.

(7-4) Evaluation of Binding Between APLNR and Antibody Using Flow Cytometry

Binding evaluation of the antibody expressed by the recombinant cells obtained in (7-3) by the same procedure as in Example 5.

Figure 8:
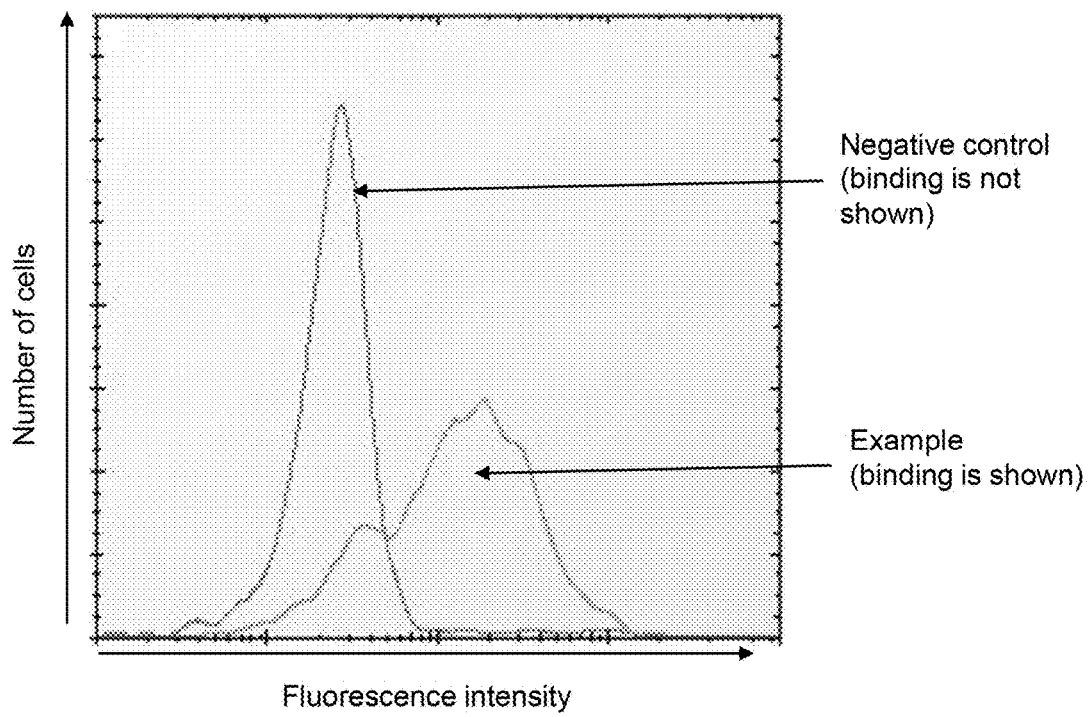
FIG. 8 is a view showing a result of a flow cytometry of a genetically recombinant antibody derived from lymphocyte recovered from a positive microwell in Example 7.

FIG. 8 shows the results of the flow cytometry. The antibody expressed by the recombinant cells obtained in (7-3) showed binding to a human APLNR-expressing CHO cell. Note here that the antibody did not show binding to a wild-type CHO cell that did not express APLNR.

Figure 9:
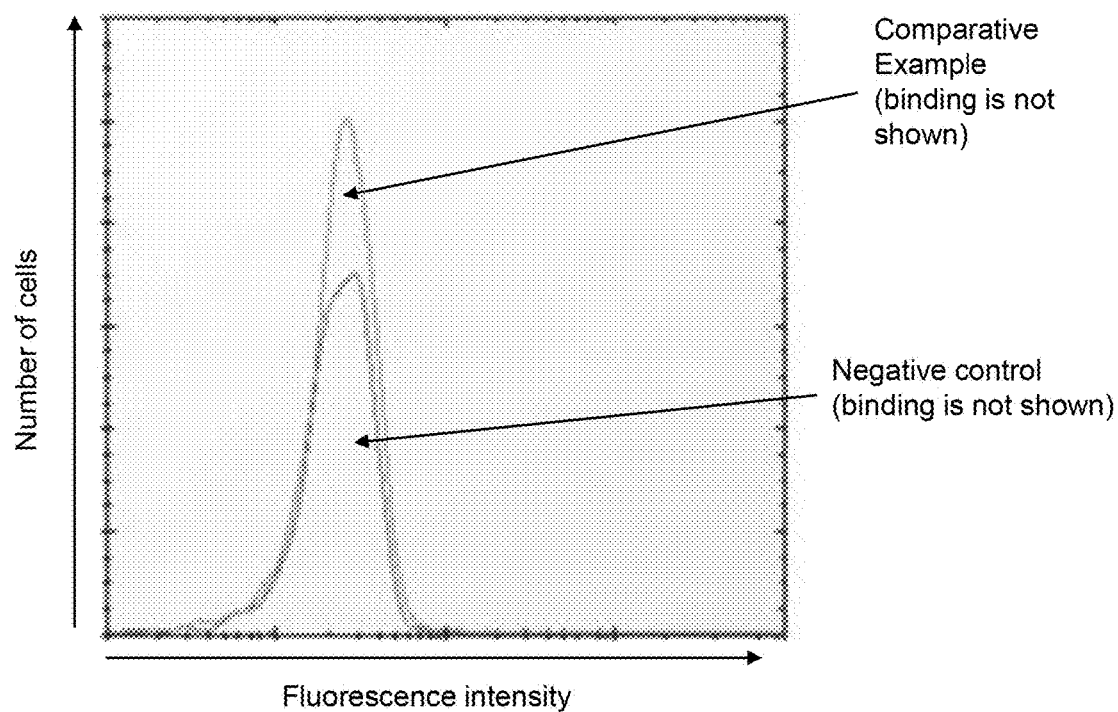
FIG. 9 is a view showing a result of a flow cytometry of a genetically recombinant antibody derived from lymphocyte recovered from a negative microwell in Example 7.

On the other hand, as shown in FIG. 9, in Comparative Example using an undesired target lymphocytes recovered from negative microwells, the antibody expressed by the recombinant cell did not show binding to the human APLNR stable expression CHO cell.

Other lymphocytes (13 types) selected in Example 6 were subjected to the similar examination. As a result, all antibodies showed binding to a human APLNR-expressing CHO cell. Furthermore, 12 of them did not show binding to a wild-type CHO cell that did not express APLNR.

From the above, it was shown that the antibody obtained in this Example had specific binding to human APLNR-expressing CHO cells.

Example 8

In order to confirm that the present invention is effective for target cell membrane proteins other than APLNR, the same experiments as in Examples 1 to 5 were performed for GPCRs using a bioactive lipid different from the ligand of APLNR as a ligand. Cells recovered from 27 microwells expected to include a positive cell were analyzed. As a result, positive cells producing an antibody having specific binding to a CHO cell expressing the target cell membrane protein were observed in 18 microwells.

From the above Examples, it was shown by the present invention that cells expressing a target substance that specifically binds to a cell membrane protein that is difficult to be purified can be selected more quickly and efficiently regardless of whether the cell is immortalized or not. In addition, it has been shown by the present invention that a specific binding substance (for example, an antibody) to a cell membrane protein can be easily produced.

Example 9

This Example shows an example of an indirect technique for visualizing a change of an intracellular signaling molecule associated with activation of cell membrane protein, occurring when a target substance specifically binds to the cell membrane protein on the surface of the first cell. A human GLP-1 (Glucagon-like peptide-1) receptor was used as a cell membrane protein, and its specific binding antibody was used as a target substance.

Human GLP-1 receptor stable expression CHO cell (first cell) produced by a method similar to the method of Example 1 was suspended in an F-12 medium (10% FBS, containing Penicillin/Streptomycin) to prepare a cell suspension having a concentration of $3\times10^4$ cells/500 μL. This cell suspension was filled in each microwell. The microchamber was centrifuged twice at 300 rpm for two minutes such that to prepare one or two first cells were stored in each microwell.

Rats were immunized in a manner similar to that in Example 2. An antibody-producing hybridoma fused to mouse myeloma was prepared in the same manner as in Example 3, and the antibody was purified from the medium. A solution prepared by diluting the purified antibody to 500 nM with an F-12 medium (containing Penicillin/Streptomycin) was prepared. To the microwell, 400 μL of this solution was added. On the other hand, similarly, a solution including no purified antibody was added to another microwell. After the addition of the solution, the cells were allowed to stand at room temperature for 30 minutes to perform a reaction of binding of the first cells with the antibody.

Thereafter, 400 μL of a ligand (GLP-1) adjusted to 500 μM with an F-12 medium (containing Penicillin/Streptomycin) was added (GLP-1 final concentration: 250 μM), and the obtained mixture was incubated at 37° C. for one hour to activate a human GLP-1 receptor. After washing the microwells with PBS, 600 μL of 4% paraformaldehyde phosphate buffer (Wako Pure Chemical Industries, Ltd.) was added and allowed to stand at room temperature for 15 minutes to immobilize the first cell. After washing the microwells with PBS again, 600 μL of ice-cooled 90% methanol was added to the microwells. Then, the microwells were allowed to stand on ice for 15 minutes to perform cell membrane permeation treatment of the first cells. After washing the microwells with PBS, 500 μL of Rabbit anti-phosphorylation-CREB (Clone 8703) antibody (Cell Signaling TECHNOLOGY) that recognizes phosphorylation of Ser133, which had been diluted 100-fold with an antibody diluent (1×PBS, 1% BSA, 0.3% Triton X-100) was added. It was allowed to stand at room temperature for one hour, and the primary antibody reaction was performed.

Alexa Fluor 488-labeled anti-rabbit IgG antibody as a fluorescence-labeled secondary antibody that detects a rabbit anti-phosphorylation-CREB antibody, and a DyLight 650-labeled anti-rat IgG antibody as a fluorescence-labeled secondary antibody that detects a rat-derived antibody were adjusted with an antibody diluent so as to be 200-fold diluted and 500-fold diluted, respectively, to prepare 500 μL of a secondary antibody solution. After completion of the primary antibody reaction, the microwells were washed with PBS and 500 μL of the prepared secondary antibody solution was added. The antibody was allowed to stand at room temperature for one hour and visualization of each antibody was performed. The microwells were washed with PBS, and then 1 mL of PBS was added thereto. The microchamber was set in the cell picking system, and signals on a transmitted light image and two types of fluorescence images were obtained. Fluorescence detection of Alexa Fluor 488 was performed under the conditions of an excitation wavelength of 482 nm and an emission wavelength of 536 nm. The fluorescence detection of the DyLight 650 was performed under the conditions of an excitation wavelength of 628 nm and an emission wavelength of 692 nm.

As a representative example, the results and discussion are described below based on the fluorescence intensities of eight microwells (No. 1 to No. 8) and the fluorescence images of two micro wells (No. 1 and No. 5). Herein, the fluorescence derived from Alexa Fluor 488 is derived from phosphorylated CREB mediated by an increase in intracellular cAMP by addition of a ligand (GLP-1). In other words, the fluorescence derived from Alexa Fluor 488 reflects presence or absence of activation of the cell membrane protein (GLP-1 receptor). When the GLP-1 receptor is activated, the fluorescence intensity from Alexa Fluor 488 is increased. On the other hand, the fluorescence derived from DyLight 650 is derived from the antibody on the surface of the first cell. In other words, the fluorescence derived from DyLight 650 reflects presence or absence of binding of the added antibody to the first cell surface. When the antibody binds to the surface of the first cell, the fluorescence intensity derived from DyLight 650 is increased.

Figure 10:
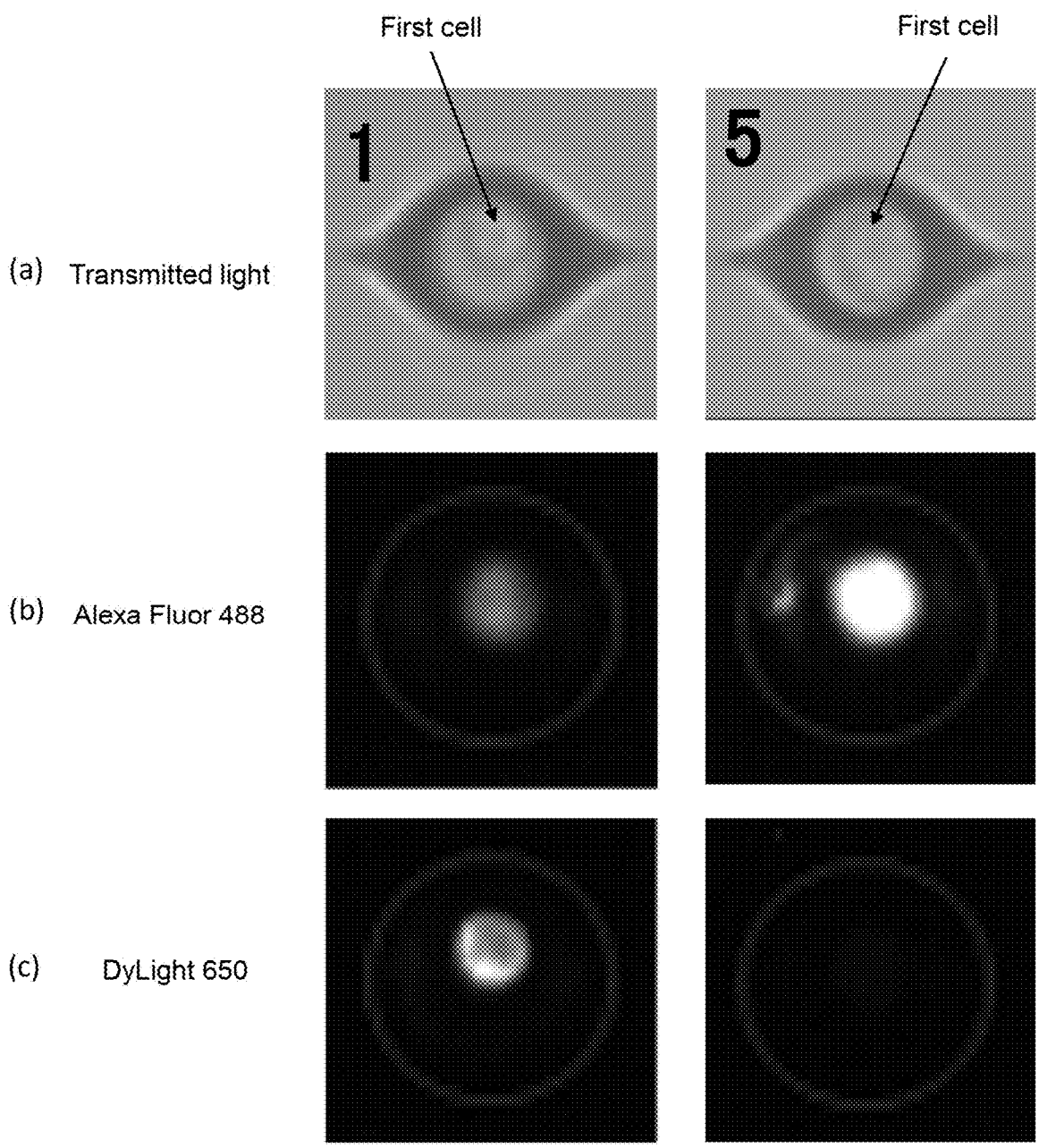
FIG. 10 is a photograph showing an example of an image of a microwell in Example 9, wherein (a) shows an observation result of transmitted light, (b) shows that of Alexa Fluor 488-derived fluorescence, and (c) shows that of DyLight 650-derived fluorescence.

Table 1 summarizes the fluorescence intensity derived from Alexa Fluor 488 and the fluorescence intensity derived from DyLight 650 for eight microwells. FIG. 10 is photographs showing images of two microwells (No. 1 and No. 5), and (a) shows an observation result of transmitted light, (b) shows that of Alexa Fluor 488-derived fluorescence, and (c) shows that of DyLight 650-derived fluorescence.

TABLE 1

| Well Number | Alexa Fluor 488 Intensity | Dylight 650 Intensity |
|---|---|---|
| 1 | 84.1 | 166.78 |
| 2 | 95.7 | 163.4 |
| 3 | 95.98 | 155.62 |
| 4 | 94.29 | 176.68 |
| 5 | 255 | 9.11 |

TABLE 1-continued

| Well Number | Alexa Fluor 488 Intensity | Dylight 650 Intensity |
|---|---|---|
| 6 | 251.12 | 9.95 |
| 7 | 237.69 | 8.79 |
| 8 | 233.66 | 9.15 |

As shown in FIG. 10(b), the fluorescence derived from Alexa Fluor 489 was weaker in the microwell of No. 1. Furthermore, as shown in Table 1, the fluorescence intensity derived from Alexa Fluor 488 in No. 1 was about ⅓ of that of No. 5 (84.1 vs. 255). This shows that in the microwell of No. 1, the GLP-1 function (activation of the GLP-1 receptor) is inhibited, while the GLP-1 function is not inhibited in the microwell of No. 5.

As shown in FIG. 10(c), the fluorescence derived from DyLight 650 was stronger in the microwell of No. 1. As shown in Table 1, the fluorescence intensity derived from DyLight 650 in No. 1 was about 18 times as that of No. 5 (166.78 vs. 9.11). This shows that in the microwell of No. 1, the added antibody strongly binds to the surface of the first cell. Furthermore, it is shown that in the microwell of No. 5, an antibody does not bind to the surface of the first cell.

Furthermore, as shown in Table 1, in the microwells in which the fluorescence intensity derived from Alexa Fluor 488 is strong, the fluorescence intensity of DyLight 650 was low (see No. 5 to No. 8). From the above-mentioned results, the relative decrease of the fluorescence intensity relative to the amount of phosphorylated CREB shows that the increase of the intracellular cAMP caused by the activation of a human GLP-1 receptor is inhibited.

The method of this Example permits identification of a microwell including an antibody that inhibits the function of the receptor by specifically binding to the human GLP-1 receptor on the surface of the first cell. Also, on the same principle, this method permits identification of a microwell including an antibody that promotes the function of the receptor. Furthermore, a second cell such as a hybridoma (for example, Example 4) or an antibody-producing lymphocyte cell (for example, Example 6) can be placed in a microwell instead of the purified antibody to identify a microwell including a target cell producing a functional antibody (target substance). Then, a target cell can be separated as a single cell from the identified microwell. The functional antibody includes both an antibody that inhibits the function of the receptor and an antibody that promotes the function of the receptor.

EXPLANATION OF REFERENCE SIGNS

1: substrate
2: microwell
3: first cell
5: second cell
6: target substance
7: label substance

The invention claimed is:

1. A method for selecting a target cell from a population of second cells, the target cell producing a target substance that specifically binds to a desired cell membrane protein, the method comprising:
   a) providing a substrate having a plurality of microwells being independent from each other without communicating with each other;
   b) introducing one first cell into each of the microwells, and allowing the first cell to adhere to each of the microwells, the first cell expressing the cell membrane protein on its surface;
   c) following the step b), introducing one second cell isolated from the population into the each of the microwells, and allowing the first cell and the second cell to coexist in the each of the microwells in a state in which the first cell and the second cell can be brought into contact with each other;
   d) following the step c), identifying a microwell including a first cell to which the target substance binds; and
   e) recovering the second cell as the target cell from the microwell identified in the step d),
   wherein the step (c) further comprises:
   incubating of the first cell and the second cell, which are allowed to coexist in each of the microwells, for a predetermined time; and
   washing each of the microwells to remove a supernatant after the incubation.

2. The method according to claim 1, wherein the step d) comprises a visualization step of visualizing binding of the target substance to the first cell.

3. The method according to claim 2, wherein the visualization step comprises adding a label substance that specifically binds to the target substance into the microwells.

4. The method according to claim 3, wherein the label substance is a labeled antibody against the target substance.

5. The method according to claim 3, wherein a label of the label substance is a fluorescent label.

6. The method according to claim 5, wherein
   the label substance is an antibody labeled with a first fluorescent substance,
   the step b) comprises a first cell labeling step of labeling the first cell adhering to the microwell with a second fluorescent substance, and
   a fluorescence wavelength of fluorescence emitted by a first fluorescent substance is different from a fluorescence wavelength of fluorescence emitted by a second fluorescent substance.

7. The method according to claim 2, wherein the visualization step comprises visualization of a change of an intracellular signaling molecule associated with activation of the cell membrane protein, occurring when the target substance binds to the first cell.

8. The method according to claim 1, wherein the first cell is a cell into which a vector expressing the cell membrane protein has been transfected.

9. The method according to claim 1, wherein the first cell is a tumor cell expressing the cell membrane protein.

10. The method according to claim 1, wherein the first cell is a non-tumor cell expressing the cell membrane protein.

11. The method according to claim 1, wherein the target substance is an antibody.

12. The method according to claim 11, wherein the second cell is derived from bone marrow, spleen, lymphatic tissue, or a blood cell derived from a non-human animal immunized with the cell membrane protein or a nucleic acid encoding the cell membrane protein.

13. The method according to claim 11, wherein the second cell is derived from human lymphatic tissue or blood.

14. The method according to claim 11, wherein the second cell is a recombinant cell including an exogenous antibody gene and expressing the antibody.

15. A method for producing a nucleic acid, the method comprising obtaining a nucleic acid encoding the target substance from a target cell selected from the population of second cells by the method according to claim 1.

16. A method for producing a recombinant cell, the method comprising:
transfecting a nucleic acid into a host cell to obtain a recombinant cell expressing a target substance,
wherein the nucleic acid encodes the target substance from a target cell selected from a population of second cells, the target cell producing the target substance that specifically binds to a desired cell membrane protein,
the target cell having been obtained by
   a) providing a substrate having a plurality of microwells being independent from each other without communicating with each other;
   b) introducing one first cell into each of the microwells, and allowing the first cell to adhere to each of the microwells, the first cell expressing the cell membrane protein on its surface;
   c) following the step b), introducing one second cell isolated from the population into the each of the microwells, and allowing the first cell and the second cell to coexist in the each of the microwells in a state in which the first cell and the second cell can be brought into contact with each other;
   d) following the step c), identifying a microwell including a first cell to which the target substance binds; and
   e) recovering the second cell as the target cell from the microwell identified in the step d),
   wherein the step (c) further comprises:
   incubating of the first cell and the second cell, which are allowed to coexist in each of the microwells, for a predetermined time; and
washing each of the microwells to remove a supernatant after the incubation.

17. A method for producing a target substance, the method comprising:
culturing a recombinant cell to obtain a cultured product, and
obtaining the target substance from the cultured product,
the recombinant cell having been produced by transfecting a nucleic acid into a host cell to obtain the recombinant cell expressing a target substance,
wherein the nucleic acid encodes the target substance from a target cell selected from a population of second cells, the target cell producing the target substance that specifically binds to a desired cell membrane protein,
the target cell having been obtained by
   a) providing a substrate having a plurality of microwells being independent from each other without communicating with each other;
   b) introducing one first cell into each of the microwells, and allowing the first cell to adhere to each of the microwells, the first cell expressing the cell membrane protein on its surface;
   c) following the step b), introducing one second cell isolated from the population into the each of the microwells, and allowing the first cell and the second cell to coexist in the each of the microwells in a state in which the first cell and the second cell can be brought into contact with each other;
   d) following the step c), identifying a microwell including a first cell to which the target substance binds; and
   e) recovering the second cell as the target cell from the microwell identified in the step d),
   wherein the step (c) further comprises:
   incubating of the first cell and the second cell, which are allowed to coexist in each of the microwells, for a predetermined time; and
washing each of the microwells to remove a supernatant after the incubation.

18. A method for producing a target substance, the method comprising culturing a target cell selected from the population of second cells by the method according to claim 1 to obtain a cultured product, and obtaining the target substance from the cultured product.

19. A method for producing a pharmaceutical composition, the method comprising combining a pharmaceutically acceptable carrier or an additive with a nucleic acid produced by the method according to claim 15 to obtain a pharmaceutical composition containing the nucleic acid as an active ingredient.

20. A method for producing a pharmaceutical composition, the method comprising combining a pharmaceutically acceptable carrier or an additive with a target substance produced by the method according to claim 17 to obtain a pharmaceutical composition containing the target substance as an active ingredient.

21. A method for producing a pharmaceutical composition, the method comprising combining a pharmaceutically acceptable carrier or an additive with a target substance produced by the method according to claim 18 to obtain a pharmaceutical composition containing the target substance as an active ingredient.

* * * * *